US008258309B2

(12) United States Patent
Harbeson et al.

(10) Patent No.: US 8,258,309 B2
(45) Date of Patent: Sep. 4, 2012

(54) AZAPEPTIDE DERIVATIVES

(75) Inventors: Scott L. Harbeson, Cambridge, MA (US); Roger D. Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 13/411,089

(22) Filed: Mar. 2, 2012

(65) Prior Publication Data

US 2012/0165288 A1 Jun. 28, 2012

Related U.S. Application Data

(63) Continuation of application No. 12/755,184, filed on Apr. 6, 2010, which is a continuation of application No. 12/157,712, filed on Jun. 12, 2008, now abandoned.

(60) Provisional application No. 60/934,201, filed on Jun. 12, 2007, provisional application No. 61/067,627, filed on Feb. 29, 2008.

(51) Int. Cl.
*A61K 31/44* (2006.01)
*C07D 213/00* (2006.01)
(52) U.S. Cl. ........................................ 546/329; 514/357
(58) Field of Classification Search ........................ None
See application file for complete search history.

(56) References Cited

U.S. PATENT DOCUMENTS

| 5,034,394 | A | 7/1991 | Daluge |
| 5,541,206 | A | 7/1996 | Kempf et al. |
| 5,849,911 | A | 12/1998 | Fassler et al. |
| 6,221,335 | B1 | 4/2001 | Foster |
| 6,440,710 | B1 | 8/2002 | Keinan et al. |
| 6,603,008 | B1 | 8/2003 | Ando et al. |
| 7,517,990 | B2 | 4/2009 | Ito et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2009/0036357 | A1 | 2/2009 | Harbeson et al. |
| 2009/0076097 | A1 | 3/2009 | Czarnik |
| 2011/0009355 | A1 | 1/2011 | Harbeson |

FOREIGN PATENT DOCUMENTS

| EP | 0206497 | 5/1986 |
| EP | 0349242 | 1/1990 |
| EP | 2003120 | 12/2008 |
| EP | 2116532 | 11/2009 |
| WO | 91/17159 | 11/1991 |
| WO | 94/14436 | 7/1994 |
| WO | 95/26325 | 10/1995 |
| WO | 97/40029 | 10/1997 |
| WO | 9746514 | 12/1997 |
| WO | 99/36404 | 7/1999 |
| WO | 03/020206 | 3/2003 |
| WO | 2005/027855 | 3/2005 |
| WO | 2005/058248 | 6/2005 |
| WO | 2005/108349 | 11/2005 |
| WO | 2006/014282 | 2/2006 |
| WO | 2006/060731 | 6/2006 |
| WO | 2007/118651 | 10/2007 |
| WO | 2008/156632 | 12/2008 |
| WO | 2010/132663 | 11/2010 |

OTHER PUBLICATIONS

Cihlar, T., et al., "Suppression of HIV-1 protease Inhibitor Resistance by Phosphonate-Mediated Solvent Anchoring," J. Mol. Biol 262: pp. 635-647 (2006). (month of publication not available).
Xu, Z., et al., "Process Research and Development for an Efficient Synthesis of the HIV Protease Inhibitor BMS-232632", Organic Process Research & Development 6: pp. 323-328 (2002). (month of publication not available).
Zhang, H., et al., "A Facile and Efficient Synthesis of d3-Labelled Reyataz," Journal of Labelled Compounds and Radiopharmaceuticals 48: pp. 1041-1047 (2005). (month of publication not available).
Kushner, D.J. et al., "Pharmacological Uses and Perspectives of Heavy Water and Deuterated Compounds," Can. J. Physiol. Pharmacol., 77:79-88 (1999). (month of publication not available).
Fisher, M.B. et al., "The Complexities Inherent in Attempts to Decrease Drug Clearance by Blocking Sites of CYP-Mediated Metabolism," Drug Discovery & Development, 9(1):101-109 (2006). (month of publication not available).
Notification of Transmittal of The International Search Report and The Written Opinion of the International Searching Authority, or The Declaration; International Search Reort; and Written Opinion of the International Searching authority for International Application No. PCT/US2008/007331, mailed Sep. 18, 2008.
European Search Report, EP Application No. 08252023.0, Dated Oct. 8, 2008.
European Examination Report, EP Application No. 08252023.0, Dated Apr. 21, 2009.
Pakistani Examination Report, Pakistani Application No. 684/2008, Date Received Jun. 30, 2009.
European Search Report, Application No. 09075359.1, dated Sep. 28, 2009.

(Continued)

*Primary Examiner* — Janet Andres
*Assistant Examiner* — Heidi Reese
(74) *Attorney, Agent, or Firm* — McCarter & English, LLP

(57) ABSTRACT

This invention relates to novel compounds that are azapeptides, and pharmaceutically acceptable salts thereof. More specifically, the invention relates to novel azapeptide compounds that are derivatives of the HIV protease inhibitor atazanavir sulfate. This invention also provides pyrogen-free compositions comprising one or more compounds of the invention and a carrier, and the use of the disclosed compounds and compositions in methods of treating diseases and conditions that are treated by administering HIV protease inhibitors. The invention also relates to the use of one or more of the disclosed compounds as reagents in analytical studies involving atazanavir.

13 Claims, 5 Drawing Sheets

OTHER PUBLICATIONS

Baillie, Thomas A., "The Use of Stable Isotopes in Pharmacological Research", Pharmacological Reviews, vol. 33 (2): 81-132 (1981).
Browne, T. R., "Stable Isotope Techniques in Early Drug Development: An Economic Evaluation", J. Clin. Pharmacol., 38: 213-220 (1998).
Cherrah, Y. et al., "Study of Deuterium Isotope Effects on Protein Binding by Gas Chromatography/Mass Spectrometry. Caffeine and Deuterated Isotopomers", Biomedical and Environmental Mass Spectrometry, 14:653-657 (1987).
Dyck, L.E., et al., "Effects of Deuterium Substitution on the Catabolism of β-Phenylethylamine: An In Vivo Study", Journal of Neurochemistry, 46(2):399-404 (1986).
Foster, A. B., "Deuterium Isotope Effects in Studies of Drug Metabolism", Trends in Pharmacological Sciences, 5:524-527 (1984).
Foster, A. B., "Deuterium Isotope Effects in the Metabolism of Drugs and Xenobiotics: Implications for Drug Design", Advances in Drug Research, 14:2-40 (1985).
Gouyette, et al., "Synthesis of Deuterium-labelled Elliptinium and its Use in Metabolic Studies", Biomedical and Environmental Mass Spectrometry, vol. 15, pp. 243-247, 1988.
Haskins, N.J., "The Application of Stable Isotopes in Biomedical Research", Biomedical Mass Spectrometry, vol. 9, No. 7, pp. 269-277, 1982.
Honma, et al., "Liberation of Deuterium from the Piperidine Ring during Hydroxylation", Drug Metabolism and Disposition, vol. 15, No. 4, pp. 551-559, 1987.
Pieniaszek, et al., "Moricizine Bioavailablity via Simultaneous, Dual, Stable Isotope Administration: Bioequivalence Implications", The Journal of Clinical Pharmacology, vol. 39, pp. 817-825, 1999.
Piliero, P., "Atazanavir: A Novel HIV-1 Protease Inhibitor," Expert Opinion Investigational drugs, 11(9): 1295-1301 (2002).
Tonn, et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes", Biological Mass Spectrometry, vol. 22, pp. 633-642, 1993.
Wolen, Robert L., "The Application of Stable Isotopes to Studies of Drug Bioabailablity and Bioequivalence", The Journal of Clinical Pharmacology, vol. 26, pp. 419-424, 1986.

FDA label for REYATAZ (atazanavir sulfate), Bristol-Myers Squibb, 16 pages, Revised Jan. 2010 from packageinserts.bms.com/pi/pi_reyataz.pdf.
European Examination Report, Application No. 09075359.1, dated Mar. 18, 2010.
Notification Concerning transmittal of International Preliminary Report on Patentability, International Application No. PCT/US2008/007331, Dated Dec. 30, 2009.
Bold, G., et al, "New Aza-Dipeptide Analogues as Potent and Orally Absorbed HIV-1 Protease Inhibitors: Candidates for Clinical Development," J. Med. Chem., 41:3387-3401 (1998).
Heine, R., et al, "Identification of Profiling of Circulating Metabolites of Atazanavir, a HIV Protease Inhibitor," Drug Metabolism and Disposition, 37:1826-1840 (2009).
Chen, R., et al, "Hypromellose Acetate Succinate," in Handbook of Pharmaceutical Excipients, 6th Ed.: Rowe, R.C., Sheskey, P.J. and Quinn, M,E., eds: pp. 330-332, Pharmaceutical Press (2009).
Fukuto, J.M., et al;. "Determinational of the Mechanism of Demethylenation of (Methylenedisoy)phenyl Compunds by Cytochrome P450 Using Deuterium Isotope Effects," J. Med. Chem., 34:2871-2876 (1991).
Gonzalez de Requena, D., et al, "Atazanavir Ctrough is associated with efficacy and safety: definition of therapeutic range," 12th Conference on Retroviruses and Opportunistic Infections, Boston USA Feb. 22-25, 2005, Poster 645.
O'Mara, E., et al., Population Pharmacodynamic (PD) Assessment of the Safety and Antiretroviral Actvity of Atazanavir (BMS-232632), 41st Interscience Conference in Antimicrobial Agents and Chemotherapy, Chicago USA Dec. 16-19, 2001, Poster 22.
The Merck Index: An Encyclopedia of Chemicals, Drugs and Biologicals, Fourteenth Edition (2006), p. 1422 (Ritonavir).
The Merck Index: An Encyclopedia of Chemicals, Drugs and Biologicals, Fourteenth Edition (2006), p. 598 (Efavirenz).
The Merck Index: An Encyclopedia of Chemicals, Drugs and Biologicals, Fourteenth Edition (2006), p. 1 (Abacavir).
The Merck Index: An Encyclopedia of Chemicals, Drugs and Biologicals, Fourteenth Edition (2006), p. 927-928 (Lamivudine).
The Merck Index: An Encyclopedia of Chemicals, Drugs and Biologicals, Fourteenth Edition (2006), p. 525 (Didanosine).

AZAPEPTIDE DERIVATIVES

RELATED APPLICATIONS

This application is a continuation application of U.S. patent application Ser. No. 12/755,184 filed on Apr. 6, 2010, which is a continuation application of U.S. patent application Ser. No. 12/157,712 filed on Jun. 12, 2008 now abandoned, which claims the benefit of U.S. Provisional Application No. 60/934,201, filed on Jun. 12, 2007 and U.S. Provisional Application No. 61/067,627, filed Feb. 29, 2008. The entire teachings of the above applications are incorporated herein by reference.

BACKGROUND OF THE INVENTION

Atazanavir sulfate, also known as (3S,8S,9S,12S)-3,12-Bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioic acid dimethyl ester, sulfate, prevents the formation of mature HIV virions in HIV-1 infected cells by selectively inhibiting the virus-specific processing of certain polyproteins (viral Gag and Gag-Pol). Atazanavir sulfate is currently approved for the treatment of HIV infection.

Atazanavir is contraindicated for coadministration with drugs that are highly dependent on CYP3A for clearance and for which elevated plasma concentrations are associated with serious and/or life-threatening events. Due to inhibition effects of atazanavir on CYP3A, CYP2C8, and UGT1A1, caution is advised when prescribing drugs primarily metabolized by CYP3A, CYP2C8, or UGT1A1 for patients receiving atazanavir. Common adverse events associated with atazanavir include hyperbilirubinemia, rash, nausea, headache, and jaundice/scleral icterus. Adverse events experienced by sonic patients and for which a causal relationship has not been established include diabetes mellitus/hyperglycemia, PR interval prolongation, hemophilia, and fat redistribution.

Despite the beneficial activities of atazanavir, there is a continuing need for new compounds to treat the aforementioned diseases and conditions.

SUMMARY OF THE INVENTION

This invention relates to novel compounds that are azapeptides, and pharmaceutically acceptable salts thereof. More specifically, the invention relates to novel azapeptide compounds that are derivatives of the HIV protease inhibitor atazanavir sulfate. This invention also provides pyrogen-free compositions comprising one or more compounds of the invention and a carrier, and the use of the disclosed compounds and compositions in methods of treating diseases and conditions that are treated by administering HIV protease inhibitors. The invention also relates to the use of one or more of the disclosed compounds as reagents in analytical studies involving atazanavir.

The compounds of the invention are represented by Formula A:

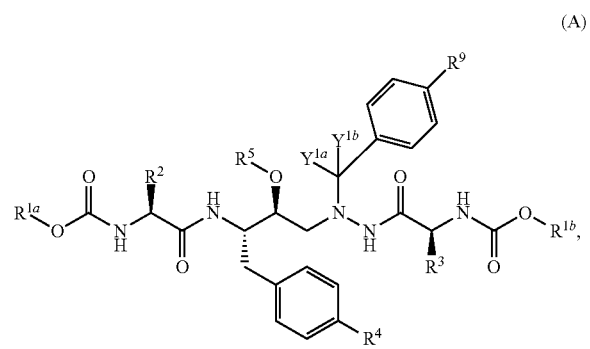

(A)

or a salt, hydrate or solvate thereof, wherein:

each of $R^{1a}$ and $R^{1b}$ is independently selected from $C_1$-$C_3$ alkyl, wherein one or more hydrogen atoms in the alkyl is optionally replaced with a deuterium atom;

each of $R^2$ and $R^3$ is independently selected from isopropyl, sec-butyl, and tert-butyl wherein one or more hydrogen atoms in the isopropyl, sec-butyl, or tert-butyl is optionally replaced with a deuterium atom;

$R^4$ is selected from H, OH and —O—$(CR^6R^7$—$O)_n$-$R^8$;

$R^5$ is selected from H and —$(CR^6R^7$—$O)_n$-$R^8$, wherein:

$R^6$ and $R^7$ are each independently selected from H, $C_1$-$C_6$ alkyl, $C_2$-$C_6$ alkenyl, $C_2$-$C_6$ alkynyl, and $C_3$-$C_7$ cycloalkyl, or $R^6$ and $R^7$ are taken together with the carbon to which they are attached to form a 3-7-membered cycloalkyl;

each $R^8$ is independently selected from —C(O)H, —C(O)—($C_1$-$C_7$ alkyl), —P(O)—$(OH)_2$, —S(O)—OH, —S(O)$_2$—OH, and A-$R^{11}$, wherein A is an α-amino acid residue; and $R^{11}$ is selected from H, $C_1$-$C_6$ alkyl, —C(O)—($C_1$-$C_7$ alkyl), A-$R^{12}$, wherein $R^{12}$ is selected from H, $C_1$-$C_6$ alkyl, and —C(O)—($C_1$-$C_7$ alkyl); and n is 0 or 1;

wherein any alkyl in $R^5$ is optionally substituted;

each of $Y^{1a}$ and $Y^{1b}$ is independently selected from H and D;

$R^9$ is selected from 2-thienyl, 3-thienyl, thiazol-5-yl, thiazol-2-yl, pyridin-2-yl, pyridin-3-yl, pyridin-4-yl, pyrazin-2-yl, 2-methyl-2H-tetrazol-5-yl, 2-($d_3$-methyl)-2H-tetrazol-5-yl, 1-methyl-1H-tetrazol-5-yl, and 1-($d_3$-methyl)-1H-tetrazol-5-yl; and at least one of $R^{1a}$, $R^{1b}$, $R^2$, $R^3$ or Y variable comprises a deuterium atom.

The compounds, pharmaceutically acceptable salts thereof and compositions of the invention are useful for treating diseases that are effectively treated by a compound that is an HIV protease inhibitor. As such, the present invention includes a method of treating a disease which is susceptible to treatment by a compound that is an HIV protease inhibitor, comprising administering to a subject in need thereof an effective amount of (i) a compound or pharmaceutically acceptable salt thereof; or (ii) a pyrogen-free composition (e.g., a pharmaceutical composition) described herein.

Diseases or conditions susceptible to treatment with a compound having HIV protease inhibitory activity include, but are not limited to, HIV infection.

The compounds and compositions of this invention are also useful as reagents in methods for determining the concentration of atazanavir sulfate in solution, examining the metabolism of atazanavir sulfate and other analytical studies. An additional utility of compounds of any of the formulae herein include their use as internal standards to determine the true concentrations atazanavir sulfate in biological matrices, such as plasma.

DETAILED DESCRIPTION OF THE INVENTION

Figure 1:
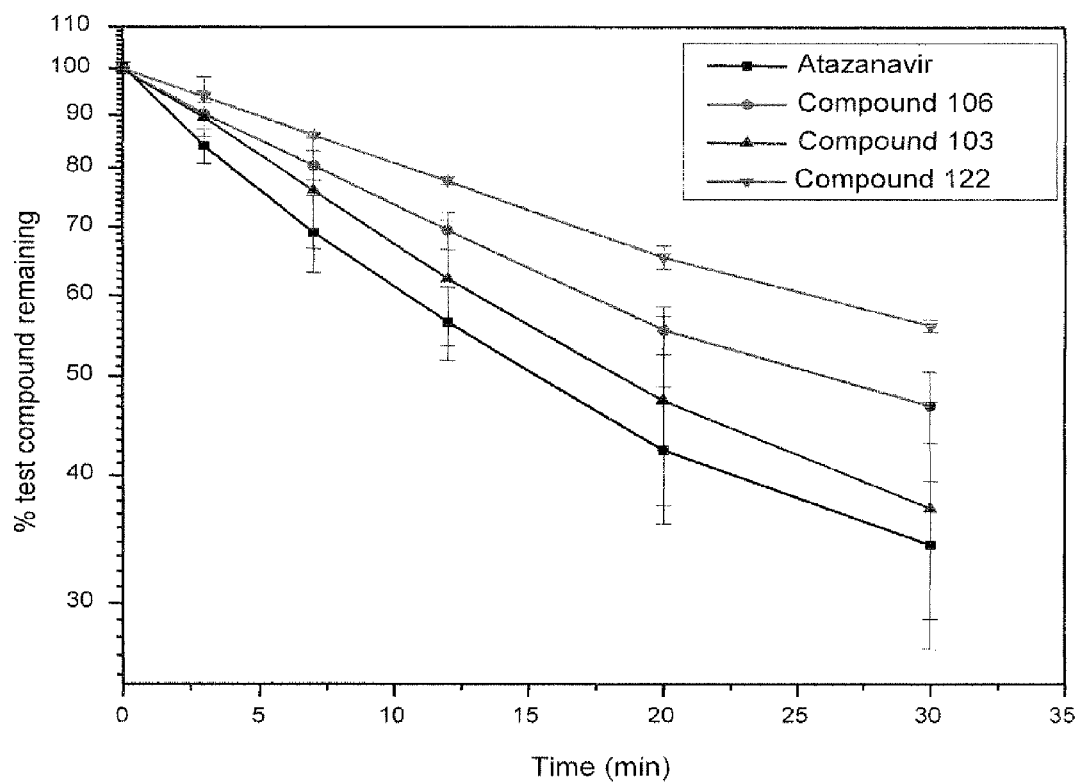
FIG. 1 is a graph showing the relative stability of compounds of this invention in human liver microsomes as compared to atazanavir.

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of atazanavir will inherently contain small amounts of deuterated isotopologues. The concentration of naturally abundant stable hydrogen isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725.

Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3500 times greater than the natural abundance of deuterium, which is 0.015% (i.e., at least 52.5% incorporation of deuterium).

The term "isotopic enrichment factor" as used herein means the ratio between the isotopic abundance of D at a specified position in a compound of this invention and the naturally occurring abundance of that isotope. The natural abundance of deuterium is 0.015%.

In other embodiments, a compound of this invention has an isotopic enrichment factor for each deuterium present at a site designated as a potential site of deuteration on the compound of at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

The term "isotopologue" refers to a species that differs from a specific compound of this invention only in the isotopic composition thereof. Isotopologues can differ in the level of isotopic enrichment at one or more positions and/or in the positions(s) of isotopic enrichment.

It will be understood that the term "compound," when referring to the compounds of the invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues will be less than 47.5% of the compound.

The term "compound" is also intended to include any solvates or hydrates thereof.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

For those compounds of the invention comprising —P(O)—(OH)$_2$, —S(O)—OH, —S(O)$_2$—OH, suitable cationic moieties to form pharmaceutically acceptable salts include, but are not limited to, alkali metals such as sodium, potassium, and lithium; alkaline earth metals such as calcium and magnesium; other metals, such as aluminum and zinc; ammonia, and organic amines, such as mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; amino acids such as arginine, lysine, and the like, and zwitterions, such as glycine and the like.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The disclosed compounds may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms.

When the stereochemistry of the disclosed compounds is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

When a disclosed compound is named or depicted by structure without indicating the stereochemistry, and has at least one chiral center, it is to be understood that the name or structure encompasses one enantiomer of the compound free from the corresponding optical isomer, a racemic mixture of the compound and mixtures enriched in one enantiomer relative to its corresponding optical isomer ("scalemic mixtures").

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "$^t$", and "t-" each refer to tertiary. "US" refers to the United States of America. "FDA" refers to Food and Drug Administration. "NDA" refers to New Drug Application.

The term "optionally substituted" refers to the optional replacement of one or more hydogen atoms with another moiety. Unless otherwise specified, any hydrogen atom including terminal hydrogen atoms, can be optionally replaced.

The term "halo" refers to any of —Cl, —F, —Br, or —I.
The term "oxo" refers to =O.
The term "alkoxy" refers to —O-alkyl.
The term "alkylamino" refers to —NH-alkyl.
The term "dialkylamino" refers to N(alkyl)-alkyl, wherein the two alkyl moieties are the same or different.

The term "alkyl" refers to straight or branched alkyl chains of from 1 to 12 carbon atoms, preferably from 1 to 8 carbon atoms, more preferably from 1 to 4 carbon atoms unless otherwise specified. Examples of straight chained and branched alkyl groups include methyl, ethyl, n-propyl, isopropyl, n-butyl, sec-butyl, tert-butyl, pentyl, hexyl, heptyl and octyl. Alkyl may be optionally substituted.

Alkyl or aryl groups that are optionally substituted will typically contain one to four substituents that are independently selected. Examples of optional substituents include $C_{1-7}$alkyl, halo, cyano, hydroxyl, carboxy, alkoxy, oxo, amino, alkylamino, dialkylamino, cycloheteroalkyl, alkylcycloheteroalkyl, aryl, alkylaryl, heteroaryl, and alkylheteroaryl.

The term "cycloheteroalkyl" refers to a non-aromatic monocyclic, bicyclic, tricyclic, spirocyclic, or tetracyclic ring system which includes one or more heteroatoms such as nitrogen, oxygen or sulfur in at least one of the rings. Each ring can be four, five, six, seven or eight-membered. Examples include tetrahydrofuryl, tetrahydrothiophenyl, morpholino, thiomorpholino, pyrrolidinyl, piperazinyl, piperidinyl, and thiazolidinyl, along with the cyclic form of sugars.

The term "alkylcycloheteroalkyl" refers to a cycloheteroalkyl group comprising an alkyl substituent. Examples include 4-methylpiperazin-1-yl and 4-methylpiperidin-1-yl.

The term "aryl" refers carbocyclic aromatic groups such as phenyl and naphthyl.

The term "alkylaryl" refers to an aryl group linked to the rest of the molecule through an alkyl chain.

The term "heteroaryl" refers to monocyclic aromatic groups comprising one or more heteroatoms such as nitrogen, oxygen or sulfur in the ring, such as imidazolyl, thienyl, furyl, pyridyl, pyrimidyl, pyranyl, pyrazolyl, pyrrolyl, pyrazinyl, thiazolyl, oxazolyl, and tetrazolyl. Heteroaryl groups also include fused polycyclic aromatic ring systems in which at least one ring comprises one or more heteroatoms such as nitrogen, oxygen or sulfur. Examples include benzothienyl, benzofuryl, indolyl, quinolinyl, benzothiazole, benzoxazole, benzimidazole, quinolinyl, isoquinolinyl and isoindolyl.

The term "alkylheteroaryl" refers to a heteroaryl group linked to the rest of the molecule through an alkyl chain.

The term "α-amino acid residue" refers to a group of the general formula —C(O)—CHR—NH— and includes naturally occurring and synthetic amino acids in either a D- or L-configuration.

Unless otherwise specified, the term "α-amino acid" includes α-amino acids having a (D)-, (L)- or racemic (D,L) configuration. It is understood that when the variable $R^8$ is an α-amino acid, it is linked to the rest of the molecule through the carbonyl carbon directly bonded to the α-carbon of the amino acid. In accordance with the structure of Formula I, such a linkage results in the formation of an ester Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

The compounds of the invention are represented by Formula A:

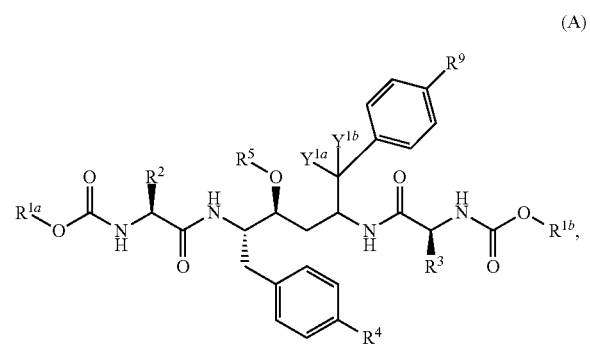

(A)

or a salt, hydrate or solvate thereof, wherein:
each of $R^{1a}$ and $R^{1b}$ is independently selected from $C_1$-$C_3$ alkyl, wherein one or more hydrogen atoms in the alkyl is optionally replaced with a deuterium atom;

each of $R^2$ and $R^3$ is independently selected from isopropyl, sec-butyl, and tert-butyl wherein one or more hydrogen atoms in the isopropyl, sec-butyl, or tert-butyl is optionally replaced with a deuterium atom;

$R^4$ is selected from H, OH and —O—$(CR^6R^7$—O$)_n$-$R^8$ $R^5$ is selected from H and —$(CR^6R^7$—O$)_n$-$R^8$, wherein:

$R^6$ and $R^7$ are each independently selected from H, $C_1$-$C_6$ alkyl, $C_2$-$C_6$ alkenyl, $C_2$-$C_6$ alkynyl, and $C_3$-$C_7$ cycloalkyl, or $R^6$ and $R^7$ are taken together with the carbon to which they are attached to form a 3-7-membered cycloalkyl;

each $R^8$ is independently selected from —C(O)H, —C(O)—($C_1$-$C_7$ alkyl), —P(O)—(OH)$_2$, —S(O)—OH, —S(O)$_2$—OH, and A-$R^{11}$, wherein A is an α-amino acid residue; and
$R^{11}$ is selected from H, $C_1$-$C_6$ alkyl, —C(O)—($C_1$-$C_7$ alkyl), A-$R^{12}$,
wherein $R^{12}$ is selected from H, $C_1$-$C_6$ alkyl, and —C(O)—($C_1$-$C_7$ alkyl); and
n is 0 or 1;
wherein any alkyl in $R^5$ is optionally substituted;
each of $Y^{1a}$ and $Y^{1b}$ is independently selected from H and D;
$R^9$ is selected from 2-thienyl, 3-thienyl, thiazol-5-yl, thiazol-2-yl, pyridin-2-yl, pyridin-3-yl, pyridin-4-yl, pyrazin-2-yl, 2-methyl-2H-tetrazol-5-yl, 2-($d_3$-methyl)-2H-tetrazol-5-yl, 1-methyl-1H-tetrazol-5-yl, and 1-($d_3$-methyl)-1H-tetrazol-5-yl; and
at least one of $R^{1a}$, $R^{1b}$, $R^2$, $R^3$ or Y variable comprises a deuterium atom.

Specific embodiments of Formula A include compounds wherein:
a) one or both of $R^2$ and $R^3$ comprise a deuterium atom;
b) each of $R^2$ and $R^3$ is independently selected from —C(CH$_3$)$_3$, —C(CD$_3$)$_3$, —CH(CH$_3$)$_2$, —CD(CD$_3$)$_2$, —CH$_2$CH$_2$(CH$_3$)$_2$, and —CD$_2$CD$_2$(CD$_3$)$_2$;
c) one or both of $R^{1a}$ and $R^{1b}$ comprise a deuterium atom;
d) each of $R^{1a}$ and $R^{1b}$ is independently selected from —CH$_3$, —CD$_3$, —CH$_2$CH$_3$, —CD$_2$CD$_3$, —CD$_2$CD$_2$CD$_3$, and —CH$_2$CH$_2$CH$_3$;
e) $R^5$ is H, P(O)—(OH)$_2$, —CH$_2$—O—P(O)—(OH)$_2$, or a pharmaceutically acceptable salt thereof;
f) $R^2$ is selected from —C(CD$_3$)$_3$, —CD(CD$_3$)$_2$, and —CD$_2$CD$_2$(CD$_3$)$_2$; or
g) two or more of the parameters set forth in a) through f) are met.

In one embodiment, the compounds of the invention are represented by Formula I:

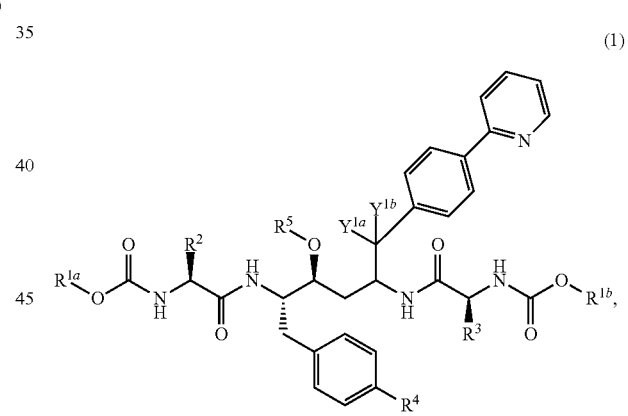

(I)

or a pharmaceutically acceptable salt thereof, wherein:
each of $R^{1a}$ and $R^{1b}$ is independently selected from CH$_3$, CH$_2$D, CHD$_2$, and CD$_3$;
each of $R^2$ and $R^3$ is independently —C(CH$_3$)$_3$, wherein from 1 to 9 hydrogen atoms are optionally replaced with a deuterium atom;
$R^4$ is selected from H, OH and —O—$(CR^6R^7$—O$)_n$-$R^8$
$R^5$ is selected from H and —$(CR^6R^7$—O$)_n$-$R^8$, wherein:
$R^6$ and $R^7$ are independently selected from H and $C_1$-$C_3$ alkyl;
each $R^8$ is independently selected from an α-amino acid, —C(O)H, —C(O)—($C_1$-$C_7$ alkyl), wherein said $C_1$-$C_7$ alkyl is optionally substituted, —P(O)—(OH)$_2$, and —S(O)—OH;
n is 0 or 1;
$Y^{1a}$ and $Y^{1b}$ are independently selected from H and D; and
at least one of $R^{1a}$, $R^{1b}$, $R^2$, $R^3$ or Y variable comprises a deuterium atom.

Specific embodiments of Formula I include a compound wherein:
i. each of $R^{1a}$ and $R^{1b}$ is independently selected from $CH_3$ and $CD_3$;
ii. each of $R^2$ and $R^3$ is independently selected from —$C(CH_3)_3$ and —$C(CD_3)_3$;
iii. $R^2$ is —$C(CD_3)_3$;
iv. $Y^{1a}$ and $Y^{1b}$ are the same;
v. each of $Y^{1a}$ and $Y^{1b}$ is deuterium;
vi. $R^4$ is selected from H and —O—$(CR^6R^7$—O$)_n$-$R^8$;
vii. $R^4$ and $R^5$ are simultaneously H;
viii. each $R^6$ and each $R^7$ is H;
ix. each $R^8$ is independently selected from an α-amino acid having (L)-configuration; —C(O)H; —C(O)—($C_1$-$C_3$ alkyl), wherein said $C_1$-$C_3$ alkyl is optionally substituted with cyano, hydroxyl, carboxy, alkoxy, amino, alkylamino, dialkylamino, cycloheteroalkyl, alkyl cycloheteroalkyl, aryl, alkylaryl, heteroaryl, and alkylheteroaryl; —P(O)—(OH)$_2$; a salt of —P(O)—(OH)$_2$, wherein the cation is selected from $Na^+$, $Mg^{2+}$, or ammonium; —S(O)—OH; and a salt of —S(O)—OH wherein the cation is selected from $Na^+$, $Mg^{2+}$, or ammonium;
x. each $R^8$ is independently selected from L-Serine; L-Lysine; L-Tyrosine; L-Valine; L-Glutamic acid; L-Aspartic acid; L-3-Pyridylalanine; L-Histidine; —C(O)H; —C(O)—($C_1$-$C_3$ alkyl); —C(O)CH$_2$OCH$_3$; —C(O)CH$_2$CH$_2$OCH$_3$; —C(O)CH$_2$CH$_2$C(O)OH; —C(O)CH$_2$CH$_2$NH$_2$; —C(O)CH$_2$CH$_2$NHCH$_3$; —C(O)CH$_2$CH$_2$N(CH$_3$)$_2$;

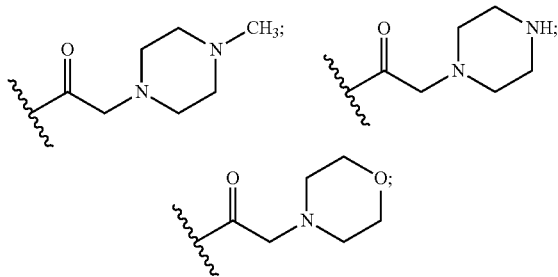

—P(O)—(OH)$_2$; a salt of —P(O)—(OH)$_2$, wherein the cation is selected from $Na^+$, $K^+$ or $Ca^{2+}$; —S(O)—OH; and a salt of —S(O)—OH, wherein the cation is selected from $Na^+$, $K^+$ or $Ca^{2+}$; or
xi. two or more of the above parameters i. through x. are met.

Example embodiments where two or more of the above parameters are met include, but are not limited to, the following particular embodiments.

In one particular embodiment, $R^2$ and $R^3$ are independently selected from —C(CH$_3$)$_3$ and —C(CD$_3$)$_3$, and $R^{1a}$ and $R^{1b}$ are independently selected from CH$_3$ and CD$_3$.

In another particular embodiment, $R^2$ is —C(CD$_3$)$_3$, and $R^{1a}$ is CD$_3$.

In another particular embodiment, $R^2$ is —C(CD$_3$)$_3$, $R^{1a}$ is CD$_3$, and $R^{1b}$ is CD$_3$.

In another particular embodiment, $Y^{1a}$ and $Y^{1b}$ are the same (i.e., both are simultaneously deuterium or simultaneously H), and either $R^{1a}$ and $R^{1b}$ are independently selected from CH$_3$ and CD$_3$, or $R^2$ and $R^3$ are independently selected from —C(CH$_3$)$_3$ and —C(CD$_3$)$_3$. In a more particular embodiment, $Y^{1a}$ and $Y^{1b}$ are the same (e.g., both are deuterium), $R^{1a}$ and $R^{1b}$ are independently selected from CH$_3$ and CD$_3$, and $R^2$ and $R^3$ are independently selected from —C(CH$_3$)$_3$ and —C(CD$_3$)$_3$.

In yet another particular embodiment, $R^4$ is selected from H and —O—$(CR^6R^7$—O$)_n$-$R^8$, and either $R^{1a}$ and $R^{1b}$ are independently selected from CH$_3$ and CD$_3$, or $R^2$ and $R^3$ are independently selected from —C(CH$_3$)$_3$ and —C(CD$_3$)$_3$. In a more particular embodiment, $R^4$ is selected from H and —O—$(CR^6R^7$—O$)_n$-$R^8$, $R^{1a}$ and $R^{1b}$ are independently selected from CH$_3$ and CD$_3$, and $R^2$ and $R^3$ are independently selected from —C(CH$_3$)$_3$ and —C(CD$_3$)$_3$.

In yet another particular embodiment, $R^4$ is selected from H and —O—$(CR^6R^7$—O$)_n$-$R^8$, and $Y^{1a}$ and $Y^{1b}$ are the same. In a more particular embodiment, $R^4$ is selected from H and —O—$(CR^6R^7$—O$)_n$-$R^8$, and $Y^{1a}$ and $Y^{1b}$ are deuterium. In another more particular embodiment, $R^4$ is selected from H and —O—$(CR^6R^7$—O$)_n$-$R^8$, $Y^{1a}$ and $Y^{1b}$ are the same (i.e., both are simultaneously deuterium or simultaneously H), and either $R^{1a}$ and $R^{1b}$ are independently selected from CH$_3$ and CD$_3$ or $R^2$ and $R^3$ are independently selected from —C(CH$_3$)$_3$ and —C(CD$_3$)$_3$. In a most particular embodiment, $R^4$ is selected from H and —O—$(CR^6R^7$—O$)_n$-$R^8$, $Y^{1a}$ and $Y^{1b}$ are the same (i.e., both are simultaneously deuterium or simultaneously H), $R^{1a}$ and $R^{1b}$ are independently selected from CH$_3$ and CD$_3$, and $R^2$ and $R^3$ are independently selected from —C(CH$_3$)$_3$ and —C(CD$_3$)$_3$.

In still another particular embodiment, $R^6$ and $R^7$ are each H, either $R^{1a}$ and $R^{1b}$ are independently selected from CH$_3$ and CD$_3$, or $R^2$ and $R^3$ are independently selected from —C(CH$_3$)$_3$ and —C(CD$_3$)$_3$. In a more particular embodiment, $R^6$ and $R^7$ are each H, $R^{1a}$ and $R^{1b}$ are independently selected from CH$_3$ and CD$_3$, and $R^2$ and $R^3$ are independently selected from —C(CH$_3$)$_3$ and —C(CD$_3$)$_3$.

In yet another particular embodiment, $R^6$ and $R^7$ are each H, and $Y^{1a}$ and $Y^{1b}$ are the same. In a more particular embodiment, $R^6$ and $R^7$ are each H, and $Y^{1a}$ and $Y^{1b}$ are deuterium. In an even more particular embodiment, $R^6$ and $R^7$ are each H, $Y^{1a}$ and $Y^{1b}$ are the same (i.e., both are simultaneously deuterium or simultaneously H), and either $R^{1a}$ and $R^{1b}$ are independently selected from CH$_3$ and CD$_3$, or $R^2$ and $R^3$ are independently selected from —C(CH$_3$)$_3$ and —C(CD$_3$)$_3$. In a most particular embodiment, $R^6$ and $R^7$ are each H, $Y^{1a}$ and $Y^{1b}$ are the same (e.g., both are deuterium), $R^{1a}$ and $R^{1b}$ are independently selected from CH$_3$ and CD$_3$, and $R^2$ and $R^3$ are independently selected from —C(CH$_3$)$_3$ and —C(CD$_3$)$_3$.

In yet another particular embodiment, $R^6$ and $R^7$ are each H, and $R^4$ is selected from H and —O—$(CR^6R^7$—O$)_n$-$R^8$. In a more particular embodiment, $R^6$ and $R^7$ are each H, $R^4$ is selected from H and —O—$(CR^6R^7$—O$)_n$-$R^8$, and either $R^{1a}$ and $R^{1b}$ are independently selected from CH$_3$ and CD$_3$ or $R^2$ and $R^3$ are independently selected from —C(CH$_3$)$_3$ and —C(CD$_3$)$_3$. In a most particular embodiment, $R^6$ and $R^7$ are each H, $R^4$ is selected from H and —O—$(CR^6R^7$—O$)_n$-$R^8$, $R^{1a}$ and $R^{1b}$ are independently selected from CH$_3$ and CD$_3$, and $R^2$ and $R^3$ are independently selected from —C(CH$_3$)$_3$ and —C(CD$_3$)$_3$.

In yet another particular embodiment, $R^6$ and $R^7$ are each H, $R^4$ is selected from H and —O—$(CR^6R^7$—O$)_n$-$R^8$, and $Y^{1a}$ and $Y^{1b}$ are the same. In a more particular embodiment, $R^6$ and each $R^7$ are each H, $R^4$ is selected from H and —O—$(CR^6R^7$—O$)_n$-$R^8$, and $Y^{1a}$ and $Y^{1b}$ are deuterium. In an even more particular embodiment, $R^6$ and $R^7$ are each H, $R^4$ is selected from H and —O—$(CR^6R^7$—O$)_n$-$R^8$, $Y^{1a}$ and $Y^{1b}$ are the same (i.e., both are simultaneously deuterium or simultaneously H), and either $R^{1a}$ and $R^{1b}$ are independently selected from CH$_3$ and CD$_3$, or $R^2$ and $R^3$ are independently selected from —C(CH$_3$)$_3$ and —C(CD$_3$)$_3$. In a most particular embodiment, $R^6$ and $R^7$ are each H, $R^4$ is selected from H and —O—$(CR^6R^7—O)_n$-$R^8$, $Y^{1a}$ and $Y^{1b}$ are the same (i.e., both are simultaneously deuterium or simultaneously H), $R^{1a}$ and $R^{1b}$ are independently selected from $CH_3$ and $CD_3$, and $R^2$ and $R^3$ are independently selected from —$C(CH_3)_3$ and —$C(CD_3)_3$.

In another set of embodiments, for any one of the above listed embodiments, $R^8$ is independently selected from an α-amino acid having (L)-configuration; —C(O)H; —C(O)—($C_1$-$C_3$ alkyl), wherein said $C_1$-$C_3$ alkyl is optionally substituted with cyano, hydroxyl, carboxy, alkoxy, amino, alkylamino, dialkylamino, cycloheteroalkyl, alkyl cycloheteroalkyl, aryl, alkylaryl, heteroaryl, and alkylheteroaryl; —P(O)—$(OH)_2$; a salt of —P(O)—$(OH)_2$ wherein the cation is selected from $Na^+$, $K^+$, or $Ca^{2+}$; —S(O)—OH; and a salt of —S(O)—OH wherein the cation is selected from $Na^+$, $K^+$, or $Ca^{2+}$.

In a further set of embodiments, for any one of the above listed embodiments, $R^8$ is independently selected from L-Serine; L-Lysine; L-Tyrosine; L-Valine; L-Glutamic acid; L-Aspartic acid; L-3-Pyridylalanine; L-Histidine; —C(O)H; —C(O)—($C_1$-$C_3$ alkyl); —C(O)$CH_2OCH_3$; —C(O)$CH_2CH_2OCH_3$; —C(O)$CH_2CH_2C(O)OH$; —C(O)$CH_2CH_2NH_2$; —C(O)$CH_2CH_2NHCH_3$; —C(O)$CH_2CH_2N(CH_3)_2$;

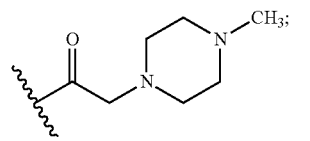

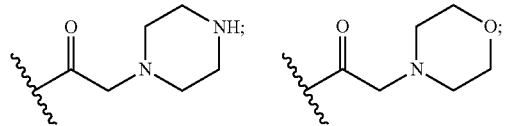

—P(O)—$(OH)_2$; a salt of —P(O)—$(OH)_2$ wherein the cation is selected from $Na^+$, $Mg^{2+}$, or ammonium; —S(O)—OH; and a salt of —S(O)—OH wherein the cation is selected from $Na^+$, $Mg^{2+}$, or ammonium; and In yet another particular embodiment, $R^4$ and $R^5$ are simultaneously H, and either $R^{1a}$ and $R^{1b}$ are independently selected from $CH_3$ and $CD_3$, or $R^2$ and $R^3$ are independently selected from —$C(CH_3)_3$ and —$C(CD_3)_3$. In a more particular embodiment, $R^4$ and $R^5$ are simultaneously H, $R^{1a}$ and $R^{1b}$ are independently selected from $CH_3$ and $CD_3$, and $R^2$ and $R^3$ are independently selected from —$C(CH_3)_3$ and —$C(CD_3)_3$.

In another particular embodiment, $R^4$ and $R^5$ are simultaneously H, and $Y^{1a}$ and $Y^{1b}$ are the same. In a more particular embodiment, $R^4$ and $R^5$ are simultaneously H, and $Y^{1a}$ and $Y^{1b}$ are simultaneously deuterium. In an even more particular embodiment, $R^4$ and $R^5$ are simultaneously H, $Y^{1a}$ and $Y^{1b}$ are the same (i.e., both are simultaneously deuterium or simultaneously H) and either $R^{1a}$ and $R^{1b}$ are independently selected from $CH_3$ and $CD_3$, or $R^2$ and $R^3$ are independently selected from —$C(CH_3)_3$ and —$C(CD_3)_3$. In a most particular embodiment, $R^4$ and $R^5$ are simultaneously H, $Y^{1a}$ and $Y^{1b}$ are the same (i.e., both are simultaneously deuterium or simultaneously H), $R^{1a}$ and $R^{1b}$ are independently selected from $CH_3$ and $CD_3$, and $R^2$ and $R^3$ are independently selected from —$C(CH_3)_3$ and —$C(CD_3)_3$.

In yet another embodiment, the compound is a compound of the Formula Ia:

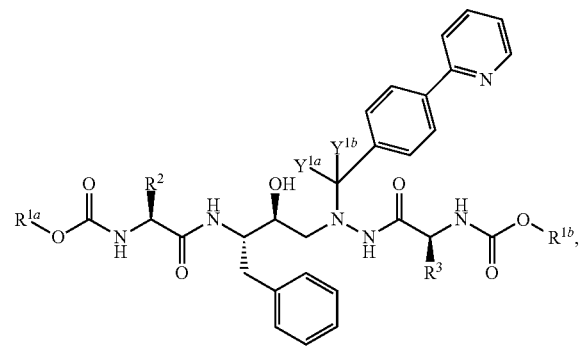

(Ia)

or a pharmaceutically acceptable salt thereof, and is selected from any one of the compounds set forth in Table 1 below.

TABLE 1

Exemplary Embodiments of Formula Ia

| Compound | $R^{1a}$ | $R^{1b}$ | $R^2$ | $R^3$ | $Y^{1a}$ | $Y^{1b}$ |
|---|---|---|---|---|---|---|
| 101 | $CD_3$ | $CH_3$ | $C(CH_3)_3$ | $C(CH_3)_3$ | H | H |
| 102 | $CH_3$ | $CD_3$ | $C(CH_3)_3$ | $C(CH_3)_3$ | H | H |
| 103 | $CD_3$ | $CD_3$ | $C(CH_3)_3$ | $C(CH_3)_3$ | H | H |
| 104 | $CH_3$ | $CH_3$ | $C(CD_3)_3$ | $C(CH_3)_3$ | H | H |
| 105 | $CH_3$ | $CH_3$ | $C(CH_3)_3$ | $C(CD_3)_3$ | H | H |
| 106 | $CH_3$ | $CH_3$ | $C(CD_3)_3$ | $C(CD_3)_3$ | H | H |
| 107 | $CH_3$ | $CH_3$ | $C(CH_3)_3$ | $C(CH_3)_3$ | D | D |
| 108 | $CD_3$ | $CH_3$ | $C(CH_3)_3$ | $C(CH_3)_3$ | D | D |
| 109 | $CH_3$ | $CD_3$ | $C(CH_3)_3$ | $C(CH_3)_3$ | D | D |
| 110 | $CD_3$ | $CD_3$ | $C(CH_3)_3$ | $C(CH_3)_3$ | D | D |
| 111 | $CH_3$ | $CH_3$ | $C(CD_3)_3$ | $C(CH_3)_3$ | D | D |
| 112 | $CH_3$ | $CH_3$ | $C(CH_3)_3$ | $C(CD_3)_3$ | D | D |
| 113 | $CH_3$ | $CH_3$ | $C(CD_3)_3$ | $C(CD_3)_3$ | D | D |
| 114 | $CD_3$ | $CH_3$ | $C(CD_3)_3$ | $C(CH_3)_3$ | H | H |
| 115 | $CD_3$ | $CH_3$ | $C(CH_3)_3$ | $C(CD_3)_3$ | H | H |
| 116 | $CD_3$ | $CH_3$ | $C(CD_3)_3$ | $C(CD_3)_3$ | H | H |
| 117 | $CH_3$ | $CD_3$ | $C(CD_3)_3$ | $C(CH_3)_3$ | H | H |
| 118 | $CH_3$ | $CD_3$ | $C(CH_3)_3$ | $C(CD_3)_3$ | H | H |
| 119 | $CH_3$ | $CD_3$ | $C(CD_3)_3$ | $C(CD_3)_3$ | H | H |
| 120 | $CD_3$ | $CD_3$ | $C(CD_3)_3$ | $C(CH_3)_3$ | H | H |
| 121 | $CD_3$ | $CD_3$ | $C(CH_3)_3$ | $C(CD_3)_3$ | H | H |
| 122 | $CD_3$ | $CD_3$ | $C(CD_3)_3$ | $C(CD_3)_3$ | H | H |
| 123 | $CD_3$ | $CH_3$ | $C(CD_3)_3$ | $C(CH_3)_3$ | D | D |
| 124 | $CD_3$ | $CH_3$ | $C(CH_3)_3$ | $C(CD_3)_3$ | D | D |
| 125 | $CD_3$ | $CH_3$ | $C(CD_3)_3$ | $C(CD_3)_3$ | D | D |
| 126 | $CH_3$ | $CD_3$ | $C(CD_3)_3$ | $C(CH_3)_3$ | D | D |
| 127 | $CH_3$ | $CD_3$ | $C(CH_3)_3$ | $C(CD_3)_3$ | D | D |
| 128 | $CH_3$ | $CD_3$ | $C(CD_3)_3$ | $C(CD_3)_3$ | D | D |
| 129 | $CD_3$ | $CD_3$ | $C(CD_3)_3$ | $C(CH_3)_3$ | D | D |
| 130 | $CD_3$ | $CD_3$ | $C(CH_3)_3$ | $C(CD_3)_3$ | D | D |
| 131 | $CD_3$ | $CD_3$ | $C(CD_3)_3$ | $C(CD_3)_3$ | D | D |

In yet another embodiment, the compound is a compound of the Formula Ib:

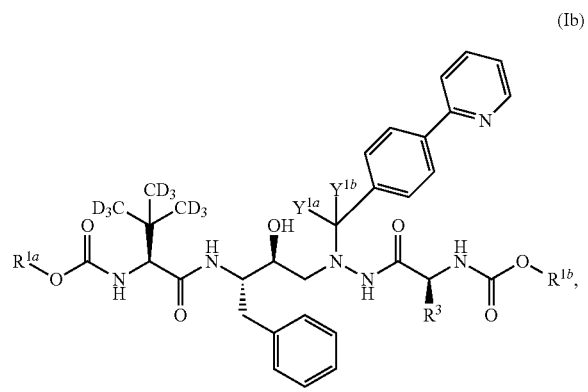

(Ib)

or a pharmaceutically acceptable salt thereof, wherein:
each of $R^{1a}$ and $R^{1b}$ is independently selected from —$CD_3$ and —$CH_3$;
$R^3$ is selected from —$C(CD_3)_3$ and —$C(CH_3)_3$; and
$Y^{1a}$ and $Y^{1b}$ are the same and are selected from H and D.

In yet another embodiment, the compound is represented by Formula Ic:

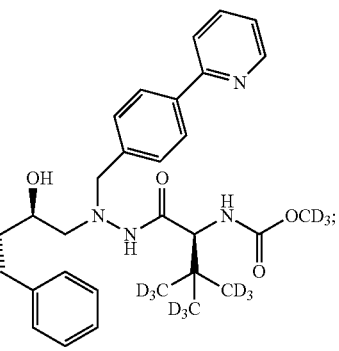

(Ic)

or a pharmaceutically acceptable salt thereof, wherein:
each of $R^{1a}$ and $R^{1b}$ is independently selected from —$CD_3$ and —$CH_3$;
$R^3$ is selected from —$C(CD_3)_3$ and —$C(CH_3)_3$;
$R^5$ is —P(O)—$(OH)_2$, —$CH_2$—P(O)—$(OH)_2$, or a pharmaceutically acceptable salt of either of the foregoing; and
$Y^{1a}$ and $Y^{1b}$ are the same and are selected from H and D.

In still another embodiment, the compound of this invention is selected from the following:

Compound 131

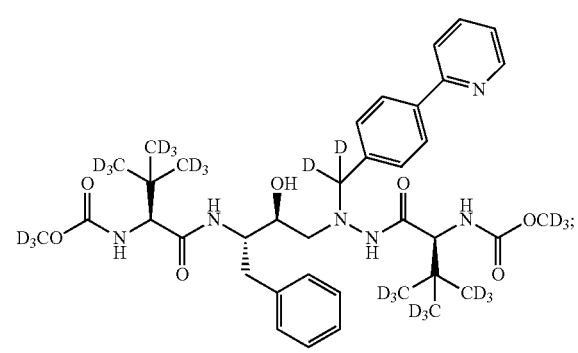

Compound 122

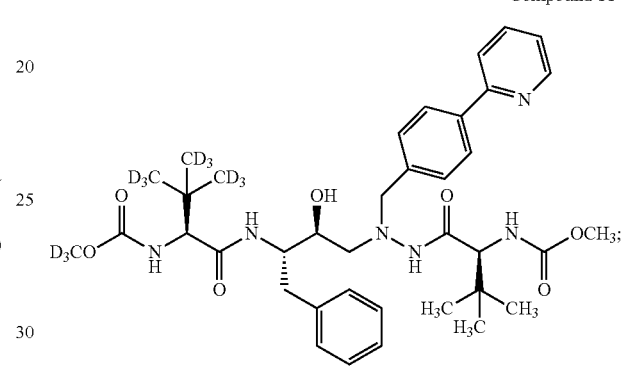

Compound 114

Compound 106

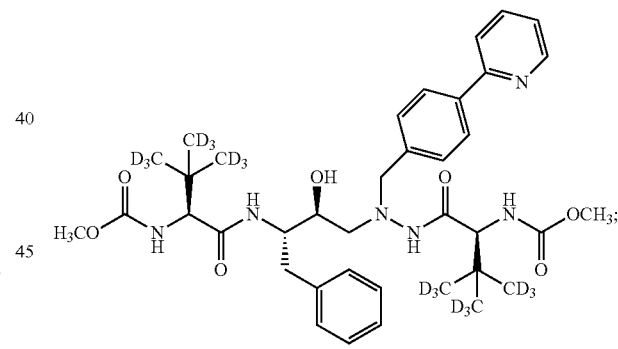

Compound 104

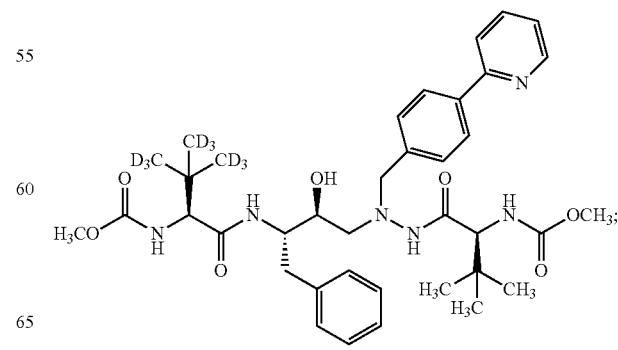

Compound 120

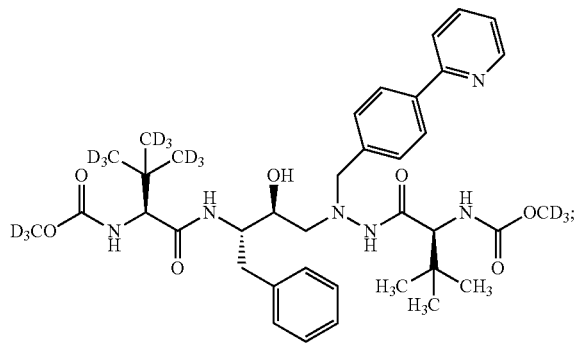

and

Compound 123

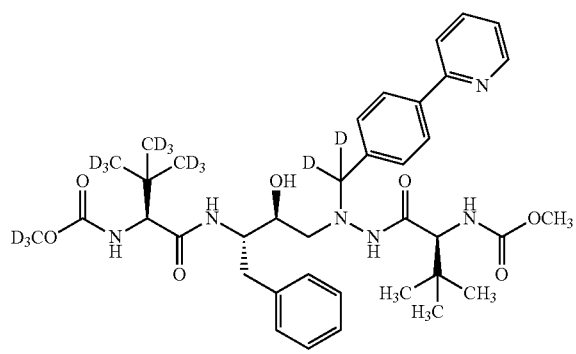

or a pharmaceutically acceptable salt of any of the foregoing.

In yet another embodiment, the compound of the invention is selected from the following:

Compound 176

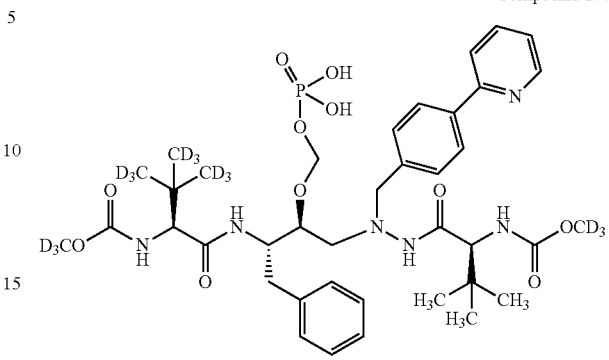

and

Compound 177

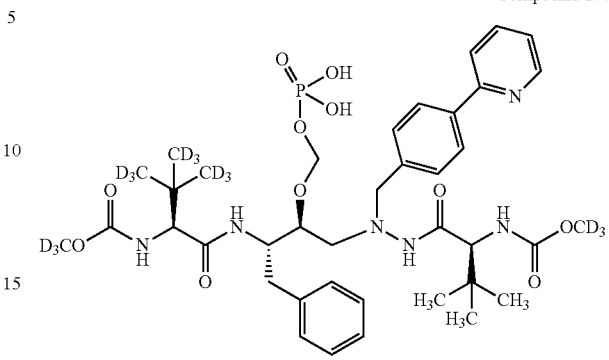

or a pharmaceutically acceptable salt of either of the foregoing.

In an even more specific embodiment, the compound is selected from Compound 114, Compound 120, Compound 122 and Compound 131.

In another set of embodiments, any atom not designated as deuterium in any of the embodiments set forth above is present at its natural isotopic abundance.

The synthesis of compounds of Formula I can be readily achieved by synthetic chemists of ordinary skill. Relevant procedures and intermediates are disclosed, for instance, in U.S. Pat. No. 5,849,911; PCT Intl Publication WO 97/46514; Bold, G et al., J Med Chem 1998, 41:3387; Xu, Z et al., Org Process Res Dev 2002, 6:323; and PCT Intl Publication WO 2006/014282.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

A convenient method for synthesizing compounds of Formula Ia is depicted in Scheme 1.

Scheme 1. General Route for Preparing Compounds of Formula Ia where $R^{1a}=R^{1b}$, $R^2=R^3$.

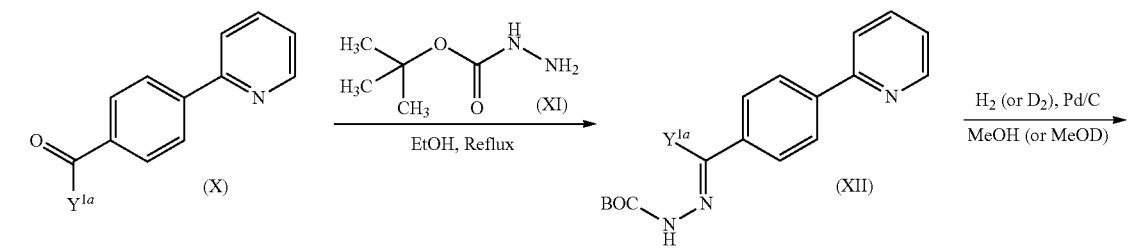

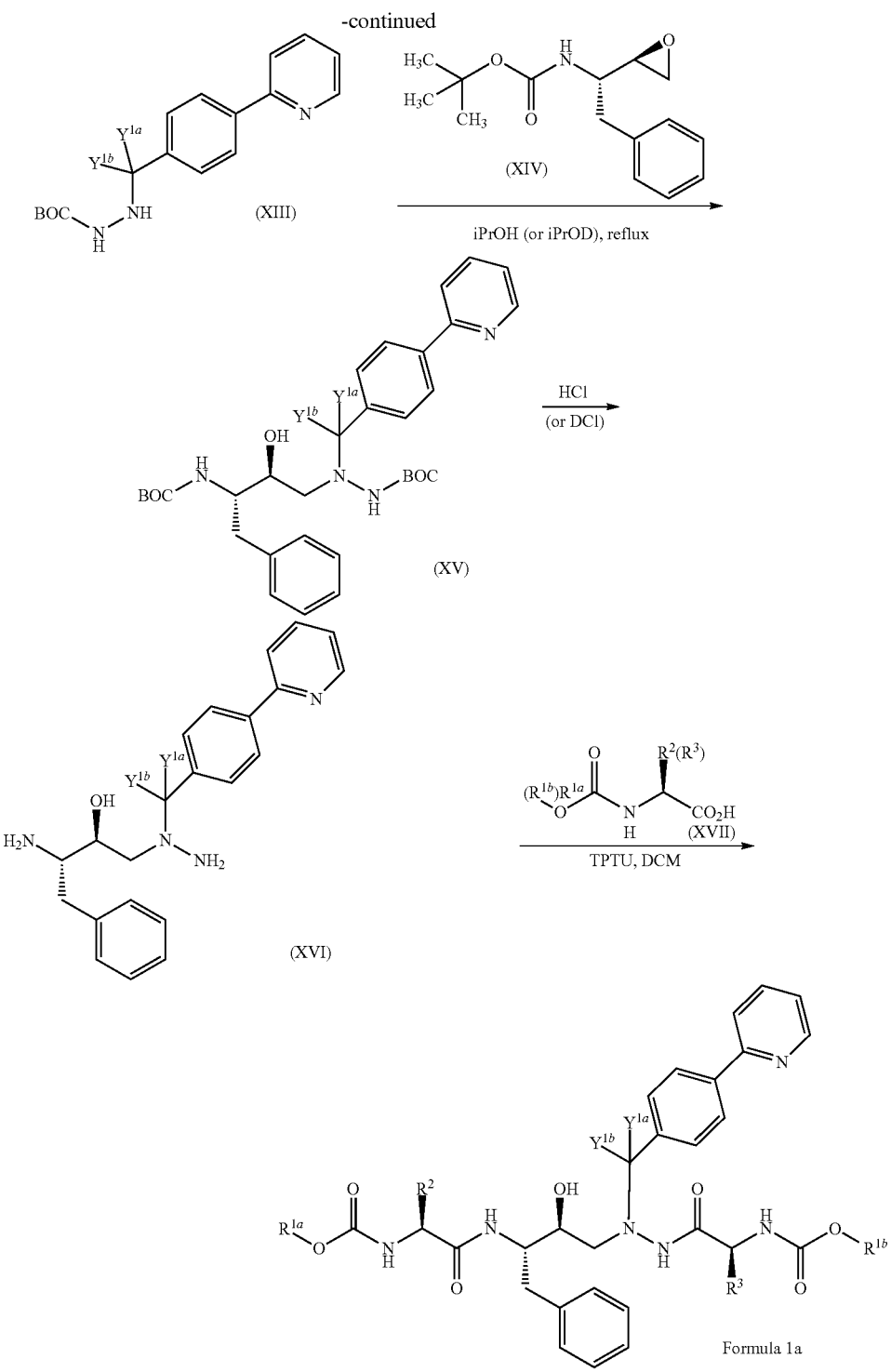

Aldehyde X is treated with the commercially available t-butoxycarbonylhydrazide (XI) to produce a BOC-protected hydrazone intermediate XII, which is then reduced using either hydrogen or deuterium gas to form the appropriate BOC-protected hydrazide XIII. The BOC-protected hydrazide XIII is then treated with the commercially available epoxide (XIV) to produce XV, which is then deprotected with hydrochloric acid to produce XVI. The appropriate carbamate derivative of tert-leucine XVII is treated with XVI in the presence of O-(1,2-dihydro-2-oxo-1-pyridyl)-N,N,N',N'-tetramethyluronium tetrafluoroborate (TPTU) to produce a compound of Formula Ia.

The use of a different protecting group on either XI or XIV together with differential deprotection, as disclosed in Zhang, H et al., J Labelled Compounds Radiopharm 2005, 48:1041-1047, allows for the synthesis of compounds of Formula Ia that are not symmetrically substituted. In this manner, different deuteration patterns for $R^{1a}$ and $R^{1b}$; and/or $R^2$ and $R^3$ can be achieved, as depicted below in Schemes 1b and 1c.

Scheme 1b. General Route where $R^{1a} \neq R^{1b}$, $R^2 \neq R^3$.
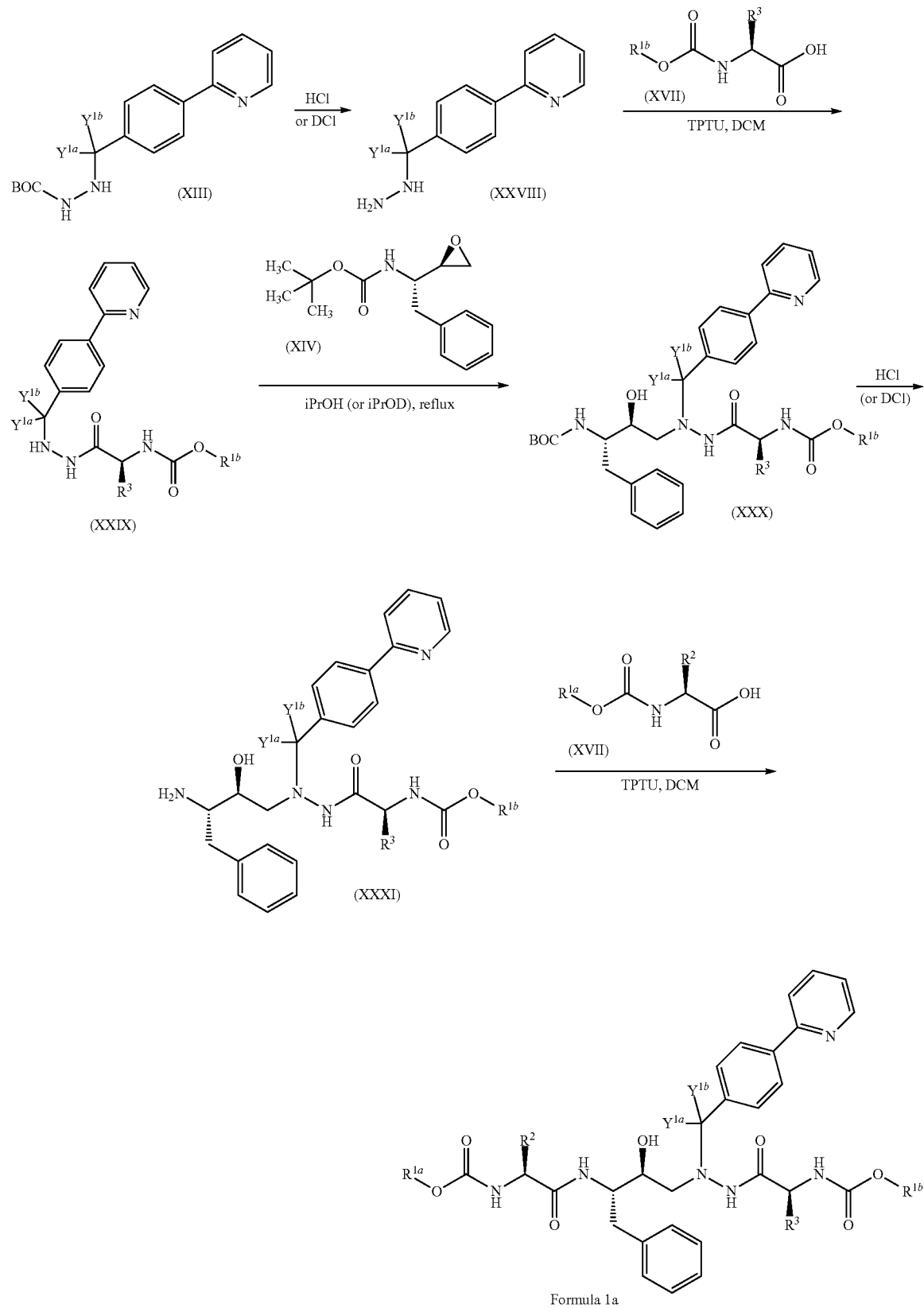
Formula 1a Scheme 1c. General Route for Incorporating Different R and Y Groups.
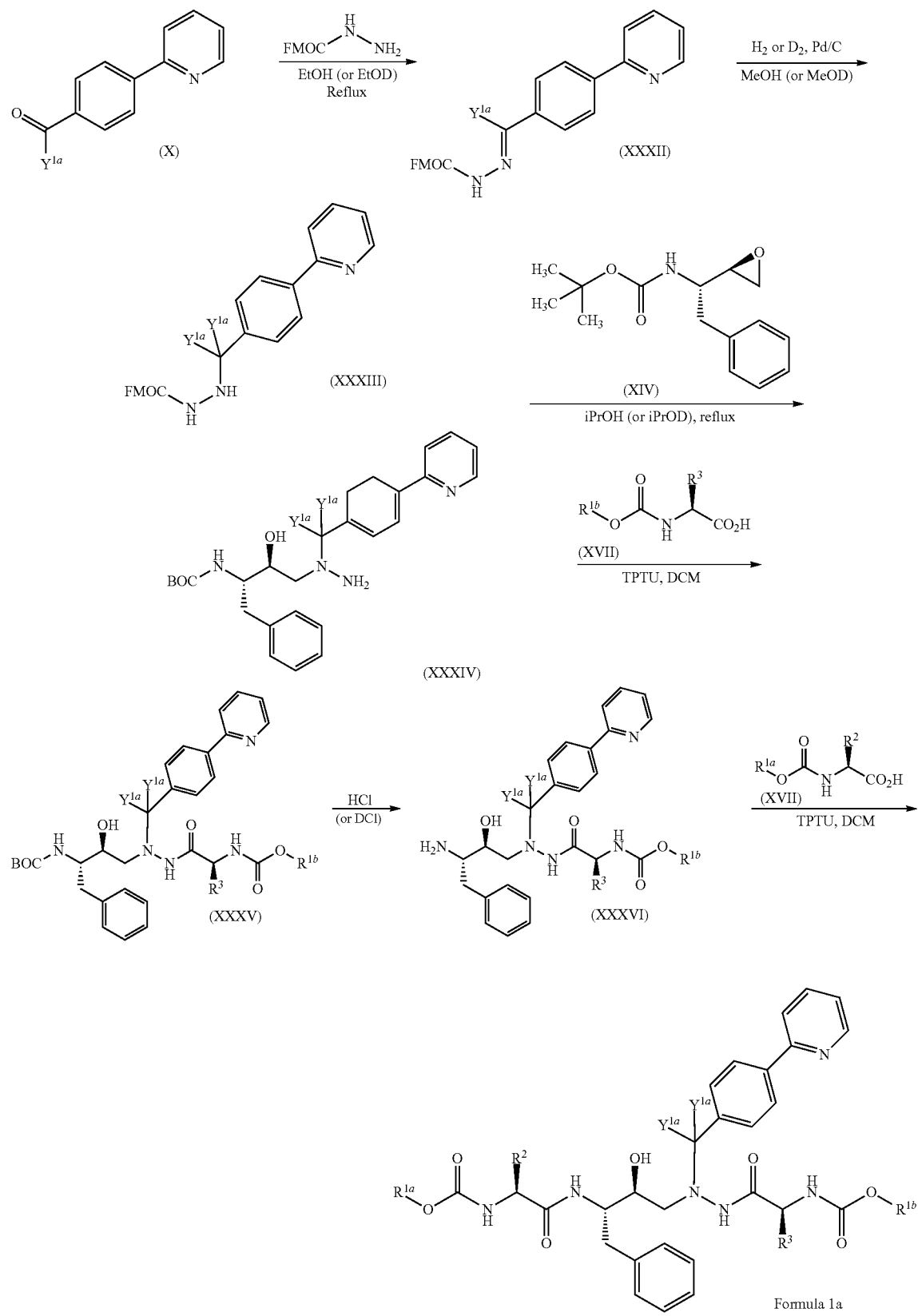

The undeuterated aldehyde X useful in Schemes 1 and 1c above is commercially available. The deuterated version of aldehyde X is synthesized according to the procedure described in Thompson, A F et al., JACS 1939, 61:1374-1376 or in Scott, C A et al., Syn Comm 1976, 6:135-139, as depicted below in Scheme 2.

Scheme 2. Preparation of Deuterated Intermediate X

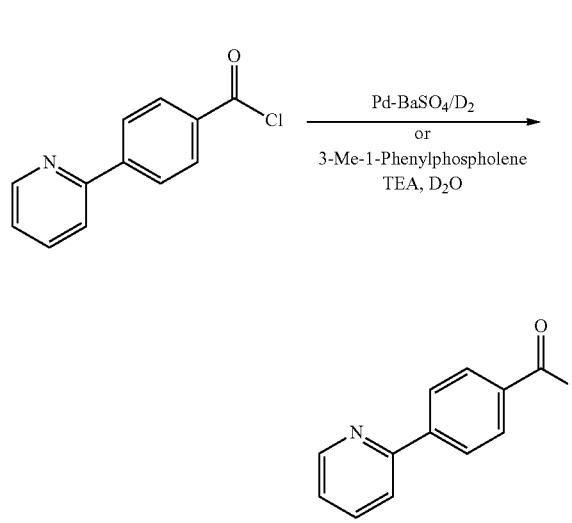

Alternatively, the undeuterated aldehyde X may be oxidized to the carboxylic acid, converted to the Weinreb amide via the acyl chloride, and reduced with LiAlD$_4$ to afford the desired deuterated aldehyde as set forth below in Scheme 2b.

Scheme 2b. Alternative Preparation of Deuterated Intermediate X.

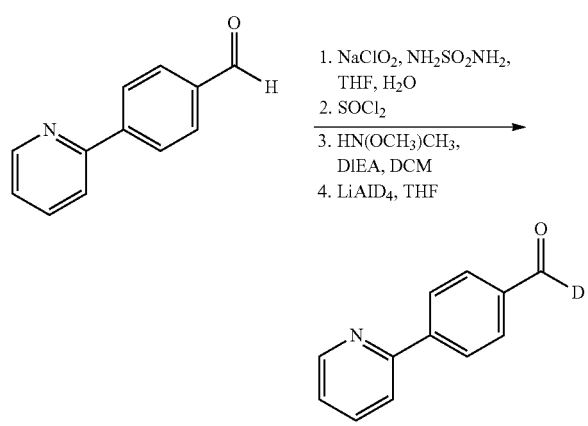

Deuterated versions of the carbamate derivative of tert-leucine XVII are produced according to Schemes 3 through 5.

Scheme 3. Route to Prepare Deuterated tert-Leucine (XIII).

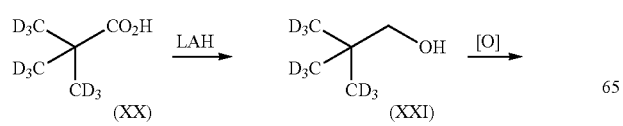

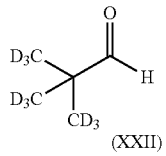

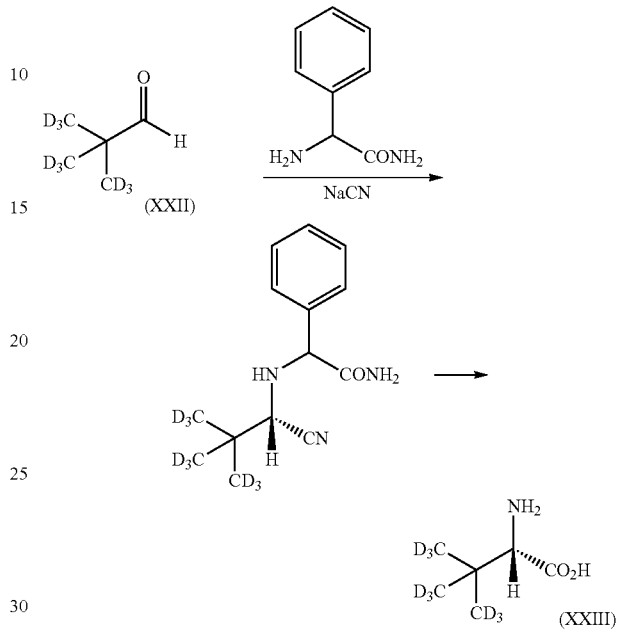

As shown in Scheme 3, tert-leucine XXIII, wherein $R^2$ and/or $R^3$ are —C(CD$_3$)$_3$, may be prepared starting from the commercially available d$_9$-pivalic acid (XX). XX is reduced to the alcohol XXI with lithium aluminum hydride as described in Brainard, R L et al., Organometallics 1986, 5:1481-1490. This alcohol XXI is oxidized to the aldehyde XXII by any one of a number of mild conditions (see, for example, Herrerias, C I et al., Tet Lett 2005, 47:13-17). The aldehyde XXII is converted to the tert-leucine XXIII using an asymmetric Strecker synthesis as disclosed by Boesten, W H J et al., Org Lett 2001, 3:1121-1124. An alternate asymmetric Strecker synthesis has been disclosed by Davis, F A et al., Org Chem 1996, 61:440-441.

Scheme 4. Conversion of Deuterated tert-Leucine to Corresponding Carbamate.

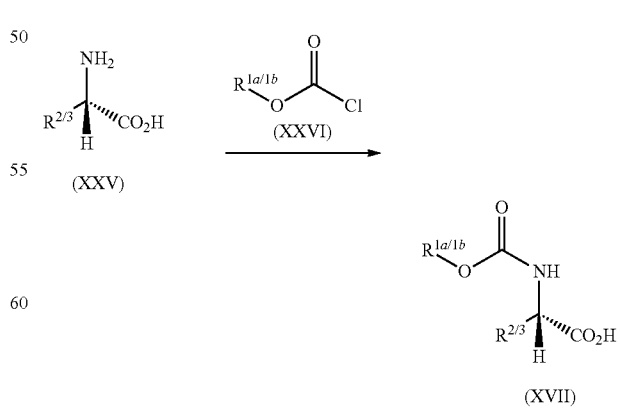

As shown in Scheme 4, deuterated tert-leucine XXV is reacted with the appropriate chloromethylformate XXVI as described in U.S. Patent Application Publication 2005131017, to produce the desired carbamate derivative of tent-leucine XVII, which is utilized in Scheme 1.

Scheme 5. Conversion of Deuterated t-Butyl Chloride to Corresponding Pivalaldehyde (XXII).

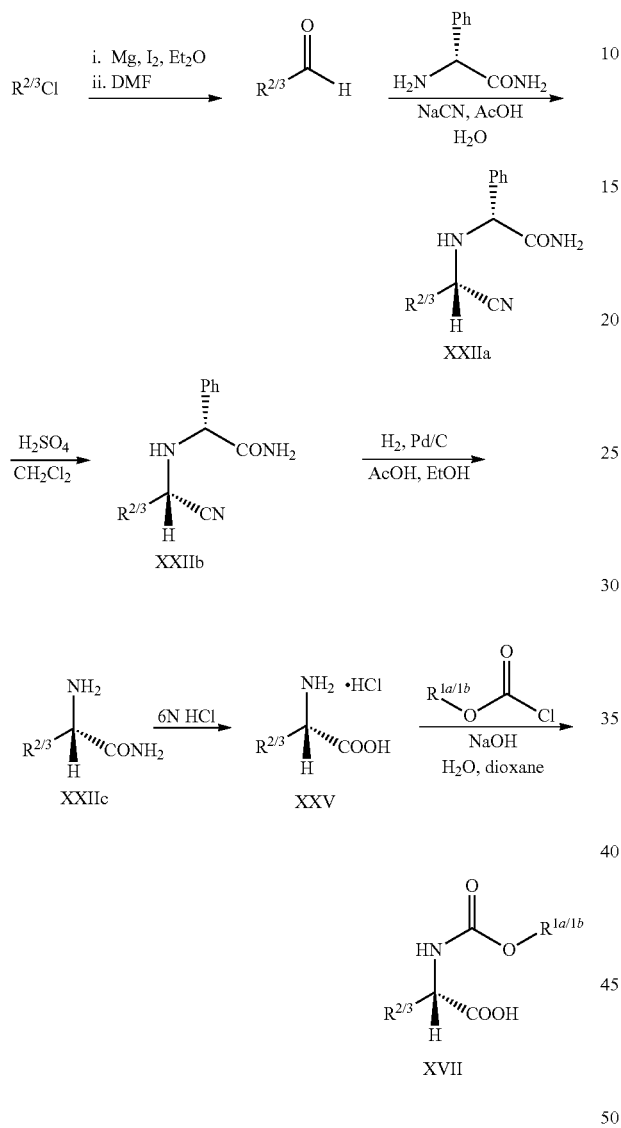

In Scheme 5, a deuterated t-butyl chloride is converted to the corresponding pivalaldehyde (XXII) by refluxing in anhydrous ether in the presence of magnesium and iodine, followed by addition of anhydrous dimethylformamide (DMF). The pivalaldehyde (XXII) is reacted with (R)-phenylglycine amide and NaCN in aqueous acetic acid to produce nitrile (XXIIa). The nitrile (XXIIa) is hydrolyzed with sulfuric acid to produce amide (XXIIb), which is then hydrogenated over palladium on carbon to produce amide (XXIIc). Amide (XXIIc) is hydrolyzed with hydrochloric acid to produce the corresponding carboxylic acid (XXV), which is then reacted with a deuterated methyl chloroformate in the presence of NaOH to produce the deuterated intermediate XVII.

A number of novel intermediates can be used to prepare compounds of Formula A. Thus, the invention also provides such a compound which is selected from the following:

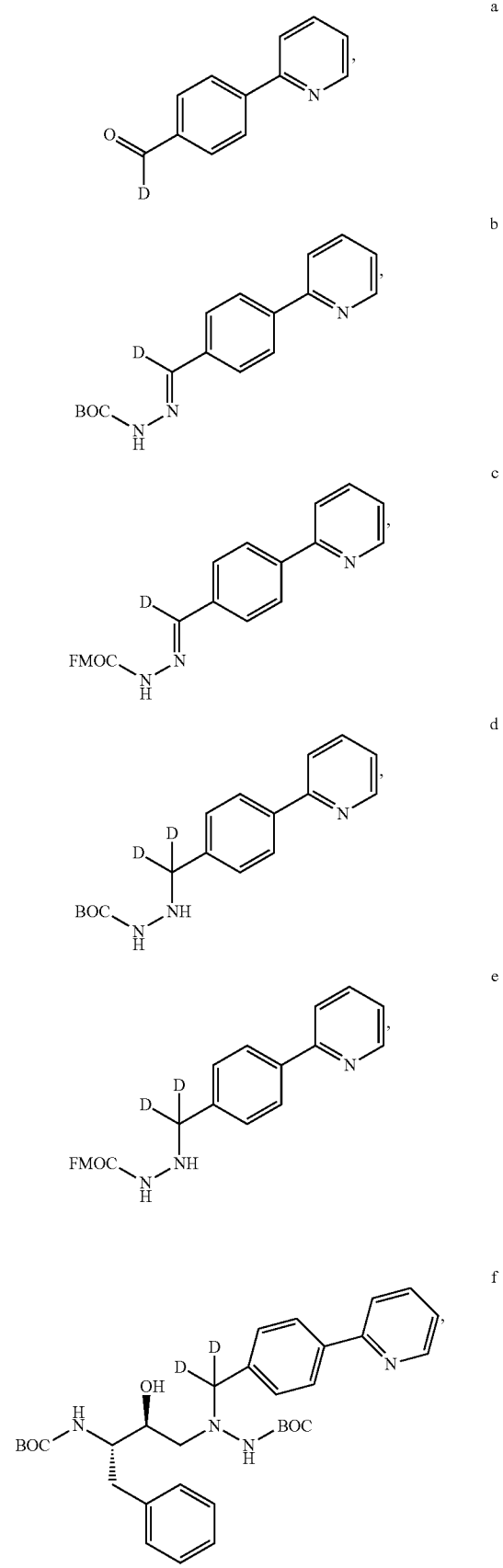

27
-continued
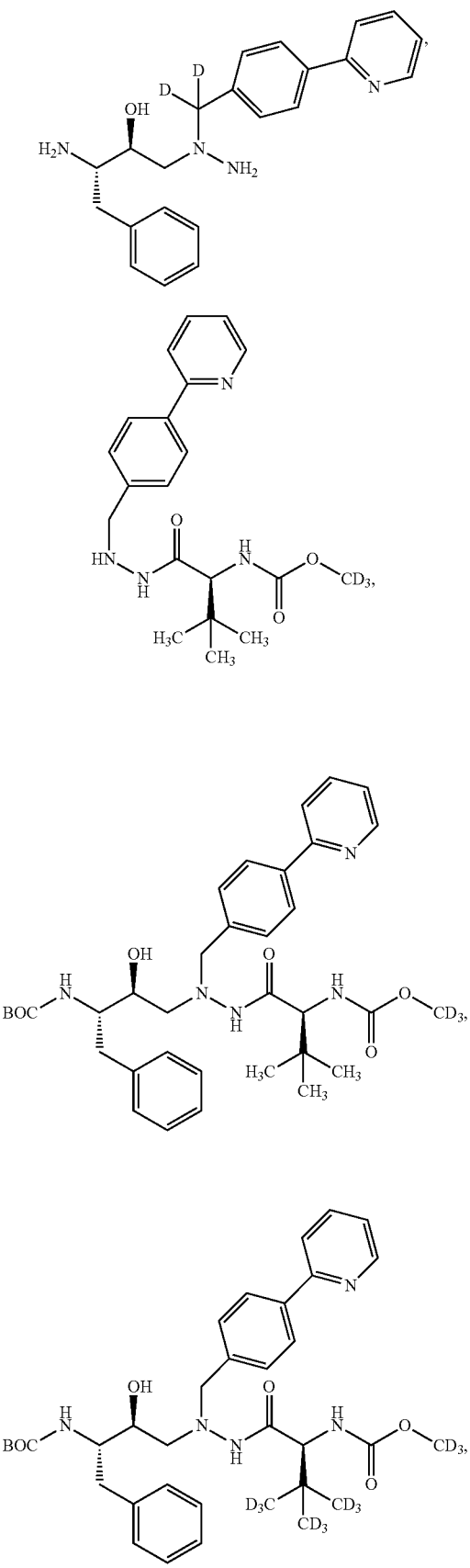
g
h
i
j
28
-continued
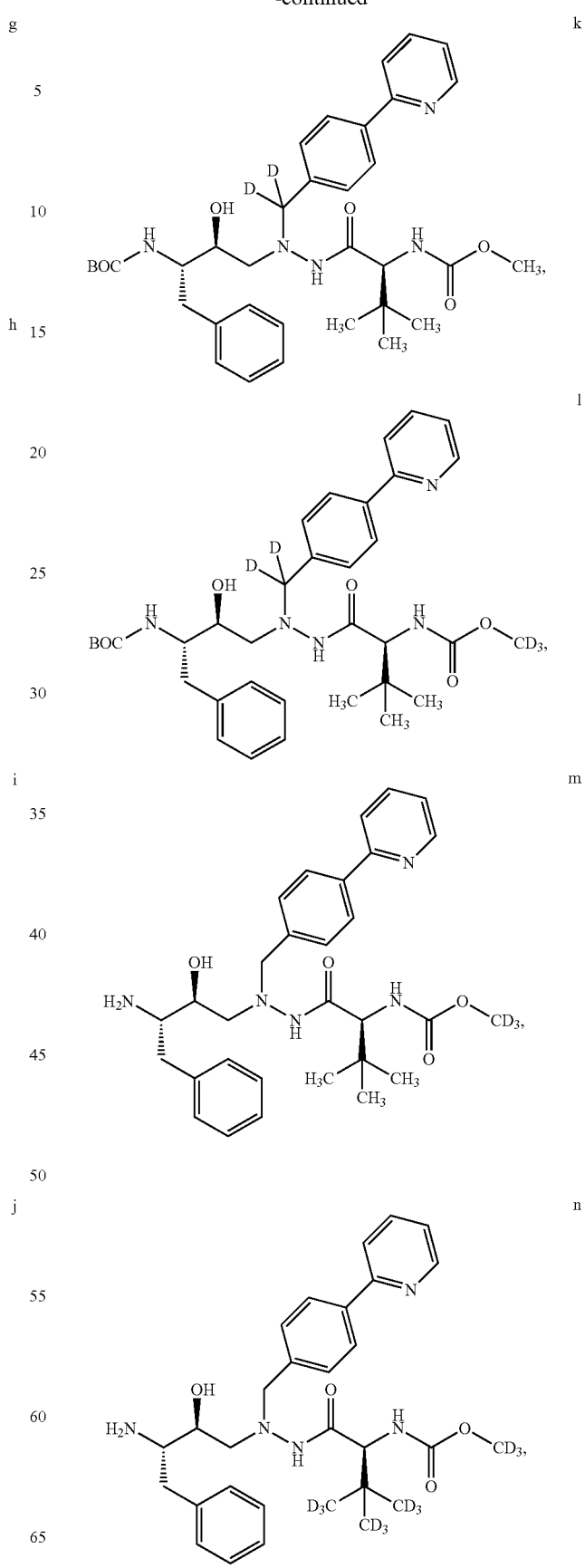
k
l
m
n

29
-continued
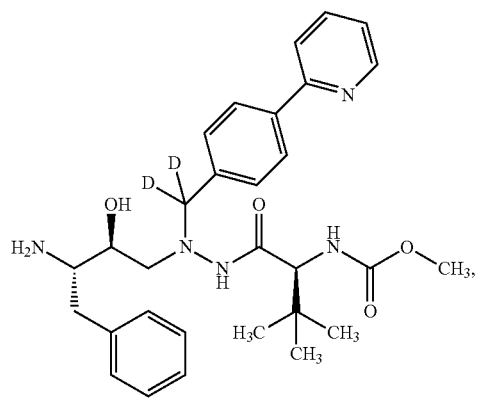
o
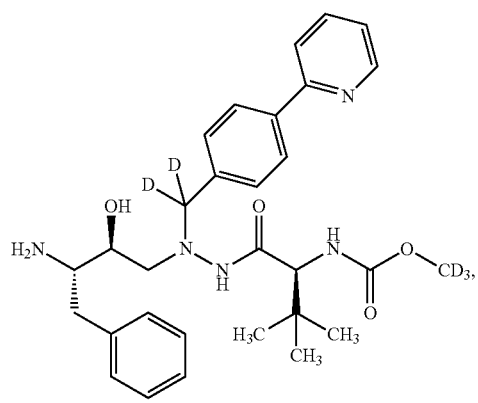
p
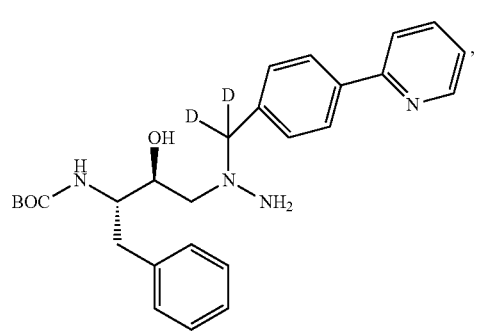
q
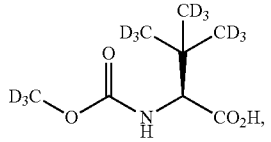
r
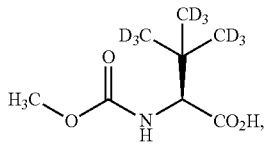
s
30
-continued
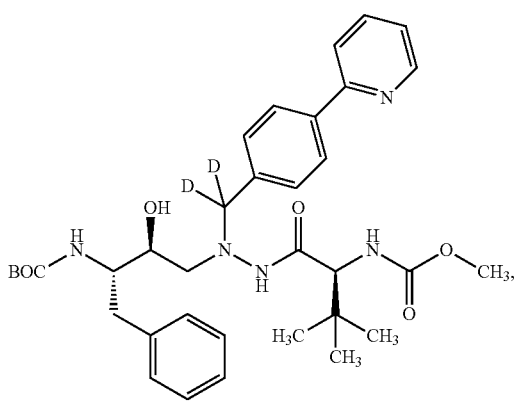
t
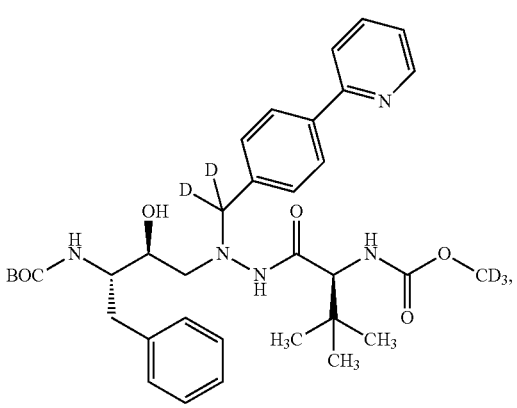
u
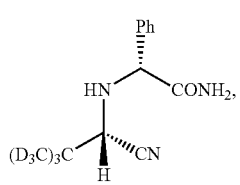
v
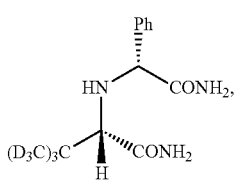
w
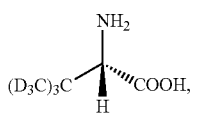
x
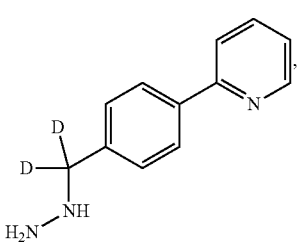
y
and

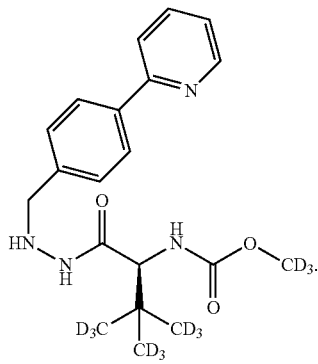

Under certain synthetic conditions, Compounds 103, 104, 106, 111, 113, 114, 120, 121, 122, 123, 129, and 131 have been prepared with an isotopic abundance at each position indicated as "D" of at least about 75%. Under other synthetic conditions, Compounds 103, 104, 106, 111, 113, 114, 120, 121, 122, 123, 129, and 131 have been prepared with an isotopic abundance at each position indicated as "D" of greater than about 95%.

Prodrugs of compounds of the invention represented by Formula A where $R^5$ is —P(O)—(OH)$_2$ or a salt thereof may be prepared according to the procedure outlined in WO 2001000635A. Prodrugs of the invention represented by Formula A where $R^5$ is —(CR$^6$R$^7$—O)$_n$-R$^8$, wherein: $R^6$ and $R^7$ are H and each $R^8$ is —P(O)—(OH)$_2$ or a salt thereof, may be prepared according to the procedures of Safadi, M et al., Pharmaceutical Research, 1993, 10(9): 1350. Other suitable methods for preparing prodrugs of the compounds of the invention can be found in PCT Intl Publication WO 2006/014282.

In other embodiments, a compound of this invention has at least 52.5% deuterium incorporation, at least 60% deuterium incorporation, at least 67.5% deuterium incorporation, at least 75% deuterium incorporation, at least 82.5% deuterium incorporation, at least 90% deuterium incorporation, or at least 95% deuterium incorporation at each position designated as deuterium in a compound of this invention. The compound of the invention may be in an amount of, for example, at least 100 mg, such as at least 20 0mg, preferably at least 400 mg, more preferably at least 500 mg and optionally up to 10 Kg.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, Val Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of any one of Formulae A, I, Ia, Ib or Ic (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and U.S. patent publications 20060094744 and 20060079502.

The pharmaceutical compositions of the invention include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the patient therapeutics may be local, so as to be administered at the site of interest. Various techniques can be used for providing the patient compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. In one embodiment, the second therapeutic agent is one or more additional compounds of the invention. In a particular embodiment, each of the two or more compounds of the invention present in such compositions differs from all others in the positions of isotopic enrichment. Commonly, such a composition comprises three, four, five or more different compounds of this invention.

In another embodiment, the second therapeutic agent may be selected from any compound or therapeutic agent known to have or that demonstrates advantageous properties when administered with a compound having the same mechanism of action as atazanavir. Such agents include those indicated as being useful in combination with atazanavir, including but not limited to, those described in PCT publications WO 2003020206, WO 2005058248, WO 2006060731 and WO 2005027855.

Preferably, the second therapeutic agent is an agent useful in the treatment or prevention of HIV infection (i.e., an antiretroviral agent).

In one embodiment, the second therapeutic agent is selected from other anti-retroviral agents including, but not limited to, a second HIV protease inhibitor (e.g., amprenavir, fosamprenavir, tipranavir, indinavir, saquinavir, lopinavir, ritonavir, darunavir, or nelfinavir), a non-nucleoside reverse transcriptase inhibitor ("NNRTI") (e.g., etravirine, delavirdine, efavirenz, nevirapine, or rilpivirine), a nucleoside/nucleotide reverse transcriptase inhibitor ("NRTI") (e.g., zidovudine, lamivudine, emtricitabine, tenofovir disoproxil fumarate, didanosine, stavudine, abacavir, racivir, amdoxovir, apricitabine, entecavir, adefovir or elvucitabine) a viral entry inhibitor (e.g., enfuvirtide, maraviroc, vicriviroc, PRO 140, or TNX-355), an integrase inhibitor (e.g., raltegravir, or elvitegravir), an immune based antiretroviral agent (e.g., immunitin, proleukin, remune, BAY 50-4798 or IR103), a viral maturation inhibitor (e.g., bevirimat), a cellular inhibitor (e.g., droxia or hydroxyurea), or combinations of two or more of the above.

In a more specific embodiment, the second therapeutic agent is selected from ritonavir, efavirenz, didanosine, tenofovir disoproxil, nelfinavir mesilate, amprenavir, raltegravir, saquinavir, lopinavir, nevirapine, emtricitabine, abacavir, lamivudine, zidovudine, maraviroc, stavudine, darunavir, fosamprenavir, vicriviroc, pharmaceutically acceptable salts of any of the foregoing, and combinations thereof.

In an even more specific embodiment, the second therapeutic agent is selected from ritonavir, efavirenz, didanosine, raltegravir, tenofovir disoproxil lamivudine, abacavir, zidovudine, emtricitabine, efavirenz, pharmaceutically acceptable salts of any of the foregoing, and combinations thereof. In another specific embodiment, the compositions of this invention comprise a compound of any one of Formulae A, I, Ia, Ib, or Ic, and two to three of the second therapeutic agents set forth above in this paragraph. In an even more specific embodiment, the compositions of this invention comprise a compound of any one of Formulae A, I, Ia, Ib, or Ic, and two of the second therapeutic agents set forth above in this paragraph.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In yet another embodiment the invention provides a pharmaceutical composition comprising an effective amount of a compound of any one of Formulae A, I, Ia, Ib or Ic, the administration of which to a test subject results in a serum terminal elimination half-life of the compound that is greater than the serum terminal elimination half-life of atazanavir when atazanavir is administered to an equivalent test subject in a pharmaceutical composition comprising a molar equivalent amount of atazanavir and that is administered in the same dosing regimen as the compound of any one of Formulae A, I, Ia, Ib or Ic. In other embodiments, the serum terminal elimination half-life of a compound of any one of Formulae A, I, Ia, Ib or Ic is at least 110%, 120%, 130%, 140%, 150% or 160% or more of the serum terminal elimination half-life of atazanavir produced by a molar equivalent atazanavir composition administered in the same dosing regimen. In a more specific embodiment, the compound of any one of Formulae A, I, Ia, Ib or Ic is administered in a single dose.

In a related embodiment, the invention provides a pharmaceutical composition comprising an effective amount of a compound of any one of Formulae A, I, Ia, Ib or Ic, or a pharmaceutically acceptable salt thereof, wherein the serum terminal elimination half-life of the compound following administration of a single dose of the composition to a test subject is greater than 5.0 hours, greater than 6.0 hours, greater than 7.0 hours or greater than 8.0 hours.

In another embodiment, the invention provides a pharmaceutical composition comprising an effective amount of a compound of any one of Formulae A, I, Ia, Ib or Ic, the administration of which to a test subject results in an $AUC_{0-\tau}$ (where $\tau$=dosing interval) of the compound that is greater than the $AUC_{0-\tau}$ of atazanavir when atazanavir is administered to an equivalent test subject in a molar equivalent pharmaceutical composition and that is administered in the same dosing regimen as the compound of any one of Formulae A, I, Ia, Ib or Ic. In other embodiments, the $AUC_{0-\tau}$ produced by a composition of this invention is at least 120%, 130%, 140%, 150%, 160% or more of the $AUC_{0-\tau}$ produced by a molar equivalent atazanavir composition administered in the same dosing regimen. In a more specific embodiment, the compound of any one of Formulae A, I, Ia, Ib or Ic is administered once-daily.

In another embodiment, the invention provides a pharmaceutical composition comprising an effective amount of a compound of any one of Formulae A, I, Ia, Ib or Ic, the oral administration of which to a test subject results in a maximum serum concentration of the compound ($C_{max}$) that is greater than the maximum serum concentration of atazanavir when atazanavir is orally administered to an equivalent test subject in a molar equivalent pharmaceutical composition and that is administered in the same dosing regimen as the compound of any one of Formulae A, I, Ia, Ib or Ic. In a related embodiment, the maximum serum concentration a compound of any one of Formulae A, I, Ia, Ib or Ic produced by oral administration of a composition of this invention is at least 120%, 125%, 130%, 135%, or more than the maximum serum concentration of atazanavir produced by oral administration of a molar equivalent atazanavir composition administered in the same dosing regimen. In a more specific embodiment, the compound of any one of Formulae A, I, Ia, Ib or Ic is administered once daily.

In another embodiment, the invention provides a pharmaceutical composition comprising an effective amount of a compound of any one of Formulae A, I, Ia, Ib or Ic, the oral administration of which to a test subject results in a minimum serum concentration of the compound ($C_{min}$) that is greater than the minimum serum concentration of atazanavir when atazanavir is orally administered to an equivalent test subject in a molar equivalent pharmaceutical composition and that is administered in the same dosing regimen as the compound of any one of Formulae A, I, Ia, Ib or Ic. In a related embodiment, the minimum serum concentration a compound of any one of Formulae A, I, Ia, Ib or Ic produced by oral administration of a composition of this invention is at least 125%, 150%, 175%, 200%, or more than the minimum serum concentration of atazanavir produced by oral administration of a molar equivalent atazanavir composition administered in the same dosing regimen. In a more specific embodiment, the compound of any one of Formulae A, I, Ia, Ib or Ic is administered once daily.

The compounds of the present invention also demonstrate greater resistance to certain metabolism as compared to atazanavir. Thus, in another embodiment, the invention provides a pharmaceutical composition comprising an effective amount of a compound of any one of Formulae A, I, Ia, Ib or Ic, the oral administration of which to a test subject results in a rate of serum clearance of the compound following oral dosing that is less than the rate of serum clearance of atazanavir following oral administration of atazanavir to an equivalent test subject in a molar equivalent pharmaceutical composition and that is administered in the same dosing regimen as the compound of any one of Formulae A, I, Ia, Ib or Ic. In other embodiments, the rate of serum clearance of a compound following oral administration of a composition of this invention is less than 90%, less than 80%, less than 70%, or less than 60% of the serum clearance rate of atazanavir following oral administration of a molar equivalent atazanavir composition administered in the same dosing regimen. In a more specific embodiment, the compound of any one of Formulae A, I, Ia, Ib or Ic is administered once daily.

In a related embodiment, the invention provides a pharmaceutical composition comprising 150 mg of a compound of any one of Formulae A, I, Ia, Ib or Ic, or a pharmaceutically acceptable salt thereof, wherein the rate of serum clearance of the compound following oral administration of a single dose of the composition to a chimpanzee is less than 90 ml/h/kg, less than 80 ml/h/kg, less than 75 ml/h/kg, or less than 70 ml/h/kg.

In another related embodiment, the invention provides a pharmaceutical composition comprising 50 mg of a compound of any one of Formulae A, I, Ia, Ib or Ic, or a pharmaceutically acceptable salt thereof, wherein the rate of serum clearance of the compound following oral administration of a single dose of the composition to a chimpanzee is less than 350 ml/h/kg, less than 325 ml/h/kg, less than 300 ml/h/kg, or less than 275 ml/h/kg.

In still another related embodiment, the invention provides a pharmaceutical composition comprising an effective amount of a compound of any one of Formulae A, I, Ia, Ib or Ic, the oral administration of which to a test subject results in an amount of compound excreted intact in 24 hours following administration that is greater than the amount of atazanavir excreted intact in 24 hours following oral administration of atazanavir to an equivalent test subject in a molar equivalent pharmaceutical composition and that is administered in the same dosing regimen as the compound of any one of Formulae A, I, Ia, Ib or Ic. In other embodiments, the amount of a compound of any one of Formulae A, I, Ia, Ib or Ic excreted intact in 24 hours following oral administration of a composition of this invention is greater than 140%, greater than 160%, greater than 180%, greater than 200%, or greater than 250% or more of the amount of atazanavir excreted intact 24 hours following oral administration of a molar equivalent atazanavir composition administered in the same dosing regimen. In a more specific embodiment, the compound of any one of Formulae A, I, Ia, Ib or Ic is administered once daily.

In yet another embodiment, the invention provides a pharmaceutical composition comprising an effective amount of a compound of any one of Formulae A, I, Ia, Ib or Ic, the administration of which to a test subject results in either a) a similar $AUC_{0-12}$, b) a similar $C_{max}$, or c) a similar $C_{min}$ (the lowest concentration within the dosing interval) as atazanavir when atazanavir is administered to an equivalent test subject in a pharmaceutical composition comprising an amount of atazanavir that is greater than the amount of the compound of any one of Formulae A, I, Ia, Ib or Ic on a mole basis of active ingredient and that is administered in the same dosing regimen as the compound of any one of Formulae A, I, Ia, Ib or Ic. In other embodiments, the effective amount of a compound of any one of Formulae A, I, Ia, Ib or Ic is no more than 80%, 70%, 60%, 50%, 40%, or less of the amount of atazanavir required to produce a similar $AUC_{0-12}$, a similar $C_{min}$ and/or a similar $C_{max}$ when administered in the same dosing regimen as the compound of any one of Formulae A, I, Ia, Ib or Ic. In a more specific embodiment, the compound of any one of Formulae A, I, Ia, Ib or Ic is administered once daily.

In another embodiment, the invention provides a pharmaceutical composition comprising between 250 mg and 275 mg of a compound of any one of Formulae A, I, Ia, Ib or Ic, the administration of which once a day to a test subject in the absence of co-administration of ritonavir results in a $C_{min}$ of between 275 and 625 ng/mL of plasma and/or a mean plasma concentration at steady state ("$C_{ss}$," also defined as $AUC_{0-\tau}$, where $\tau$ is the time of the dosing interval) of between 925 and 1425 ng/mL of plasma.

In another embodiment, the invention provides a pharmaceutical composition comprising between 275 mg and 300 mg of a compound of any one of Formulae A, I, Ia, Ib or Ic, the administration of which once a day to a test subject results in a $C_{min}$ of between 300 and 675 ng/mL of plasma and/or a $C_{ss}$ of between 1000 and 1550 ng/mL of plasma.

In another embodiment, the invention provides a pharmaceutical composition comprising between 300 mg and 325 mg of a compound of any one of Formulae A, I, Ia, Ib or Ic, the administration of which once a day to a test subject results in a $C_{min}$ of between 350 and 750 ng/mL of plasma and/or a $C_{ss}$ of between 1100 and 1675 ng/mL of plasma.

In another embodiment, the invention provides a pharmaceutical composition comprising between 325 mg and 350 mg of a compound of any one of Formulae A, I, Ia, Ib or Ic, the administration of which once a day to a test subject in the absence of co-administration of ritonavir results in a $C_{min}$ of between 375 and 800 ng/mL of plasma and/or a $C_{ss}$ of between 1200 and 1800 ng/mL of plasma.

In another embodiment, the invention provides a pharmaceutical composition comprising between 350 mg and 375 mg of a compound of any one of Formulae A, I, Ia, Ib or Ic, the administration of which once a day to a test subject in the absence of co-administration of ritonavir results in a $C_{min}$ of between 400 and 850 ng/mL of plasma and/or a $C_{ss}$ of between 1300 and 1925 ng/mL of plasma.

In another embodiment, the invention provides a pharmaceutical composition comprising between 375 mg and 400 mg of a compound of any one of Formulae A, I, Ia, Ib or Ic, the administration of which once a day to a test subject in the absence of co-administration of ritonavir results in a $C_{min}$ of between 425 and 900 ng/mL of plasma and/or a $C_{ss}$ of between 1400 and 2050 ng/mL of plasma.

In another embodiment, the invention provides a pharmaceutical composition comprising between 400 mg and 425 mg of a compound of any one of Formulae A, I, Ia, Ib or Ic, the administration of which once a day to a test subject in the absence of co-administration of ritonavir results in a $C_{min}$ of between 450 and 975 ng/mL of plasma and/or a $C_{ss}$ of between 1500 and 2175 ng/mL of plasma.

In another embodiment, the invention provides a pharmaceutical composition comprising between 425 mg and 450 mg of a compound of any one of Formulae A, I, Ia, Ib or Ic, the administration of which once a day to a test subject in the absence of co-administration of ritonavir results in a $C_{min}$ of between 500 and 1025 ng/mL of plasma and/or a $C_{ss}$ of between 1575 and 2300 ng/mL of plasma.

In each of the above embodiments, a pharmaceutically acceptable salt of a compound of any one of Formulae A, I, Ia, Ib or Ic, and/or atazanavir may be used instead of the free base form.

In a more specific embodiment, in each of the compositions set forth above, the compound is a compound of Formula I. In an even more specific embodiment, in each of the compositions set forth above, the compound is a compound of Formula Ib. In a still more specific embodiment, in each of the compositions set forth above, the compound is selected from Compound 114, Compound 120, Compound 122, and Compound 131

The term "molar equivalent amount" as used herein means an amount present in a first composition that is the same as the amount present in a second composition on a mole basis of active ingredient.

A "test subject" is any mammal, preferably a chimpanzee or a human.

An "equivalent test subject" is defined herein as being of the same species and sex as the test subject, and which shows no more than 10% variability as compared to the test subject in the pharmacokinetic parameter being tested after administration of an equal amount of atazanavir to both the test subject and the equivalent subject. The skilled artisan will recognize that one way of reducing variability is to co-dose the compound of the invention along with atazanavir.

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 200 to about 800 mg per treatment. In more specific embodiments, the range is from about 250 mg to about 600 mg, or from about 250 mg to about 400 mg, or from about 300 mg to about 500 mg, or most specifically from about 325 mg to about 450 mg. Treatment is typically administered from one to two times daily. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for atazanavir.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of treating HIV infection in a patient in need thereof comprising the step of administering to the patient an effective amount of compound of any one of Formulae A, I, Ia, Ib or Ic or a pharmaceutically acceptable composition comprising a compound of any one of Formulae A, I, Ia, Ib or Ic.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with atazanavir. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of any one of Formulae A, I, Ia, Ib or Ic and a second HIV protease inhibitor (e.g., amprenavir, fosamprenavir, tipranavir, indinavir, saquinavir, lopinavir, ritonavir, darunavir, or nelfinavir), a non-nucleoside reverse transcriptase inhibitor ("NNRTI") (e.g., etravirine, delavirdine, efavirenz, nevirapine, or rilpivirine), a nucleoside/nucleotide reverse transcriptase inhibitor ("NRTI") (e.g., zidovudine, lamivudine, emtricitabine, zidovudine, tenofovir disoproxil fumarate, didanosine, stavudine, abacavir, racivir, amdoxovir, apricitabine, or elvucitabine) a viral entry inhibitor (e.g., enfuvirtide, maraviroc, vicriviroc, PRO 140, or TNX-355), an integrase inhibitor (e.g., raltegravir, or elvitegravir), an immune based antiretroviral agent (e.g., immunitin, proleukin, remune, BAY 50-4798 or IR103), a viral maturation inhibitor (e.g., bevirimat), a cellular inhibitor (e.g., droxia or hydroxyurea), or combinations of two or more of the above.

In a more specific embodiment, the combination therapies of this invention include co-administering a compound of any one of Formulae A, I, Ia, Ib or Ic and a second therapeutic agent selected from ritonavir, efavirenz, didanosine, tenofovir disoproxil, nelfinavir mesilate, amprenavir, raltegravir, saquinavir, lopinavir, nevirapine, emtricitabine, abacavir, lamivudine, zidovudine, maraviroc, stavudine, darunavir, fosamprenavir, vicriviroc, pharmaceutically acceptable salts of any of the foregoing, and combinations thereof to treat HIV infection in a patient in need thereof.

In an even more specific embodiment, the second therapeutic agent is selected from ritonavir, efavirenz, didanosine, raltegravir, tenofovir disoproxil lamivudine, abacavir, zidovudine, emtricitabine, efavirenz, pharmaceutically acceptable salts of any of the foregoing, and combinations thereof. In another specific embodiment, the method comprises co-administering a compound of any one of Formulae A, I, Ia, Ib, or Ic, and two to three of the second therapeutic agents set forth above in this paragraph. In an even more specific embodiment, the method comprises co-administering a compound of any one of Formulae A, I, Ia, Ib, or Ic, and two of the second therapeutic agents set forth above in this paragraph.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In treatment-naïve patients, the recommended dose of Reyataz® (atazanavir sulfate) for the treatment of HIV-1 infection is 400 mg once daily with food. When co-administered with tenofovir, the recommended dose is Reyataz 300 mg and ritonavir 100 mg. In treatment-experienced patients, the recommended dose of Reyataz for the treatment of HIV-1 infection is 300 mg with ritonavir 100 mg once daily with food. Based on the animal data disclosed herein, certain compounds of this invention, following a once daily dose in the range of 325 mg to 450 mg, are expected to have the advantage in humans of achieving a $C_{min}$ and/or AUC that is comparable to the $C_{min}$ and/or AUC achieved with a once-daily dose of 300 mg dose of atazanavir boosted with 100 mg ritonavir. Accordingly, one embodiment of this invention provides a method of treating HIV infection by administering to a subject in need thereof a composition comprising a compound of this invention at a once daily dose in the range of 325 mg to 450 mg. In one embodiment, such a composition is administered without co-administration of ritonavir.

Another embodiment relates to a method of treating HIV infection by administering a composition comprising a compound of this invention at a once daily dose in the range of 250 mg to 400 mg.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of any one of Formulae A, I, Ia, Ib or Ic for use in the treatment or prevention in a patient of a disease, disorder or symptom thereof delineated herein. In a further aspect, the compounds of the invention may be used in medicine, such as in therapy. In any of these uses, the compound is preferably administered without co-administration of ritonavir.

Diagnostic Methods and Kits

The compounds and compositions of this invention are also useful as reagents in methods for determining the concentration of atazanavir in solution or biological sample such as plasma, examining the metabolism of atazanavir and other analytical studies.

According to one embodiment, the invention provides a method of determining the concentration, in a solution or a biological sample, of atazanavir, comprising the steps of
a) adding a known concentration of a compound of Formula A to the solution of biological sample;
b) subjecting the solution or biological sample to a measuring device that distinguishes atazanavir from a compound of Formula A;
c) calibrating the measuring device to correlate the detected quantity of the compound of Formula A with the known concentration of the compound of Formula A added to the biological sample or solution; and
d) measuring the quantity of atazanavir in the biological sample with said calibrated measuring device; and
e) determining the concentration of atazanavir in the solution of sample using the correlation between detected quantity and concentration obtained for a compound of Formula A.

Measuring devices that can distinguish atazanavir from the corresponding compound of Formula A include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula A comprising the steps of contacting the compound of Formula A with a metabolizing enzyme source for a period of time and comparing the amount of the compound of Formula A with the metabolic products of the compound of Formula I after the period of time.

In a related embodiment, the invention provides a method of evaluating the metabolic stability of a compound of Formula A in a patient following administration of the compound of Formula A. This method comprises the steps of obtaining a serum, urine or feces sample from the patient at a period of time following the administration of the compound of Formula A to the subject; and comparing the amount of the compound of Formula A with the metabolic products of the compound of Formula A in the serum, urine or feces sample.

The present invention also provides kits for use to treat HIV infection. These kits comprise (a) a pharmaceutical composition comprising a compound of any one of Formulae A, I, Ia, Ib or Ic or a salt thereof, wherein said pharmaceutical composition is in a container; and (b) instructions describing a method of using the pharmaceutical composition to treat HIV infection.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

The invention now being generally described, it will be more readily understood by reference to the following examples which are included merely for purposes of illustration of certain aspects and embodiments of the present invention, and are not intended to limit the invention in any way.

EXAMPLES

Example 1

Synthesis of 1,14-Di(methyl-$d_3$)(3S,8S,9S,12S)-3,12-bis[(1,1-dimethylethyl)-$d_9$]-8-hydroxy-4,11-dioxo-9-(phenylmethyl)-6-[[4-(2-pyridinyl)phenyl]methyl]-2,5,6,10,13-pentaazatetradecanedioate (Compound 122)

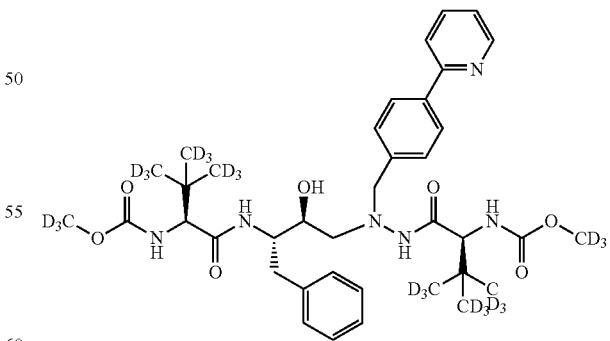

Compound 122

Compound 122 was prepared according to Scheme 1, above. The details of each step in the synthesis are set forth below and referred to as General Method A.

Synthesis of tert-butyl 2-(4-(pyridin-2-yl)benzylidene)hydrazinecarboxylate (XII, $Y^{1a}$=H). A mixture of 4-(pyridin-2-yl)benzaldehyde X (17.7 g, 96.6 mmol) and tert-butyl carbazate (12.2 g, 92.3 mmol) in ethanol (125 mL) was kept at reflux under nitrogen for 4 hours (hrs). The reaction mixture was cooled to 40° C. and ice (60 g) was added. The resulting mixture was stirred for 20 minutes (min). The precipitate was collected by filtration, washed with water and dried in a vacuum oven (60° C.) to give the product XII, wherein $Y^{1a}$=H (25.0 g, 91.1%).

Synthesis of tert-butyl 2-(4-(pyridin-2-yl)benzyl)hydrazinecarboxylate (XIII, $Y^{1a}$=$Y^{1b}$=H). A solution of XII, $Y^{1a}$=H (23.15 g, 77.85 mmol) in methanol (350 mL) was treated with 20% palladium on activated carbon (2.3 g, 50% wet) and hydrogenated at 10 psi for 4 hrs. The reaction mixture was filtered through Celite, the filter cake was washed with methanol and the solvent was removed in a rotary evaporator. The residue was recrystallized from heptane and dried in a vacuum oven (40° C.) to give XIII, wherein $Y^{1a}$=$Y^{1b}$=H (22.48 g, 96.5%).

Synthesis of tert-butyl 2-((2S,3S)-3-(tert-butoxycarbonylamino)-2-hydroxy-4-phenylbutyl)-2-(4-(pyridin-2-yl)benzyl)hydrazinecarboxylate (XV, $Y^{1a}$=$Y^{1b}$=H). A mixture of tert-butyl (S)-1((R)-oxiran-2-yl)-2-phenylethylcarbamate XIV (1.18 g, 4.48 mmol), XIII, $Y^{1a}$=$Y^{1b}$=H (1.23 g, 4.11 mmol) and isopropanol (15 mL) was kept at reflux under nitrogen overnight. The solvent was removed in a rotary evaporator and the residue was purified by chromatography on silica (100 g) with 8:2 dichloromethane/ethyl acetate to give product XV, wherein $Y^{1a}$=$Y^{1b}$=H (1.74 g, 75%).

Synthesis of (2S,3S)-3-amino-4-phenyl-1-(1-(4-(pyridin-2-yl)benzyl)hydrazinyl)butan-2-ol (XVI, $Y^{1a}$=$Y^{1b}$=H). A solution of XV, $Y^{1a}$=$Y^{1b}$=H (2.84 g, 5.05 mmol) in dichloromethane (30 mL) was stirred under nitrogen at room temperature and treated with 4N HCl in dioxane (60 mL). Stirring was continued at room temperature for 20 minutes. Sufficient methanol was added to dissolve the formed precipitate and stirring was continued at room temperature for 2 hrs. The solvents were removed in a rotary evaporator and the residue was dried in a vacuum oven (60° C.) to give XVI, wherein $Y^{1a}$=$Y^{1b}$=H (3.27 g, 5.05 mmol assuming complete conversion) as a multiple hydrochloride salt.

Synthesis of 1,14-Di(methyl-$d_3$)(3S,8S,9S,12S)-3,12-bis[(1,1-dimethylethyl)-$d_9$]-8-hydroxy-4,11-dioxo-9-(phenylmethyl)-6-[[4-(2-pyridinyl)phenyl]methyl]-2,5,6,10,13-pentaazatetradecanedioate (122). A mixture of (S)-2-(methoxycarbonylamino)-3,3-dimethylbutanoic acid XVII-$d_{12}$ ($R^{1a}$=$R^{1b}$=$CD_3$, $R^2$=$R^3$=$C(CD_3)_3$; 0.90 g, 4.44 mmol; prepared according to Scheme 5 and Example 13) and O-(1,2-dihydro-2-oxo-1-pyridyl)-N,N,N',N'-tetramethyluronium tetrafluoroborate (TPTU) (1.32 g, 4.44 mmol) in dichloromethane (40 mL) was treated with diisopropylethylamine (1.16 g, 8.88 mmol) and stirred under nitrogen at room temperature for 30 min. This solution was added to an ice-cold suspension of XVI, $Y^{1a}$=$Y^{1b}$=H, hydrochloride (1.15 g, 1.78 mmol) and the resulting solution was stirred at room temperature overnight. The reaction mixture was diluted with dichloromethane (140 mL), washed with water (2×100 mL) and saturated sodium bicarbonate solution (150 mL), dried over sodium sulfate and filtered. The solvent was removed in a rotary evaporator and the crude product was purified by chromatography on silica (120 g) with 2% ethanol in 1:1 heptane/ethyl acetate (4.5 L). The solvent was removed from the pure fractions and the residue (0.57 g) was taken in ethyl acetate (10 mL), stirred at 60° C. for 20 min and diluted with MTBE (60 mL). After cooling, the precipitate was collected by filtration, washed with MTBE and dried in a vacuum oven (55° C.) to give Compound 122 (0.40 g). Less pure fractions resulting from chromatography gave an additional 0.57 g impure material. $^1$H-NMR (300 MHz, CDCl$_3$): δ 2.54 (d, 1H), 2.87-2.95 (m, 3H), 3.57 (d, 2H), 3.75 (d, 1H), 3.91-4.08 (m, 3H), 4.81 (bs, 1H), 5.15-5.30 (m, 2H), 6.38-6.43 (m, 2H), 7.14-7.23 (m, 6H, partially obscured by CDCl$_3$), 7.41 (d, 2H), 7.68-7.76 (m, 2H), 7.94 (d, 2H), 8.68 (d, 1H). HPLC (method: 20 mm C18-RP column-gradient method 2-95% Acetonitrile+0.1% formic acid in 3.3 min with 1.7 min hold at 95% Acetonitrile; Wavelength: 254 nm): retention time: 3.22 min. MS (M+H$^+$): 729.6.

Example 2

Synthesis of 1,14-Dimethyl(3S,8S,9S,12S)-3,12-bis[(1,1-dimethylethyl)-$d_9$]-8-hydroxy-4,11-dioxo-9-(phenylmethyl)-6-[[4-(2-pyridinyl)phenyl]methyl]-2,5,6,10,13-pentaazatetradecanedioate (Compound 106)

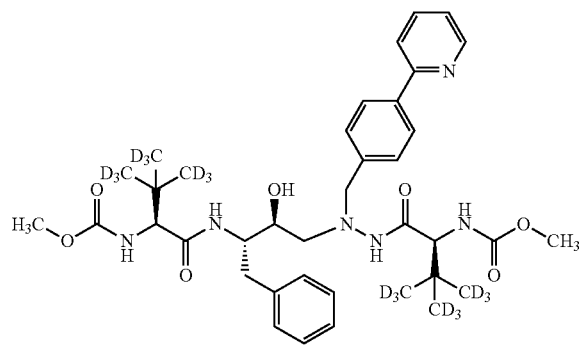

Compound 106

Compound 106 was prepared according to Scheme 1, above, following the General Method A described above.

Synthesis of 1,14-Dimethyl(3S,8S,9S,12S)-3,12-bis[(1,1-dimethylethyl)-$d_9$]-8-hydroxy-4,11-dioxo-9-(phenylmethyl)-6-[[4-(2-pyridinyl)phenyl]methyl]-2,5,6,10,13-pentaazatetradecanedioate (106). Compound 106 was prepared via General Method A above from (2S,3S)-3-amino-4-phenyl-1-(1-(4-(pyridin-2-yl)benzyl)hydrazinyl)butan-2-ol (XVI, $Y^{1a}$=$Y^{1b}$=H, hydrochloride) and (S)-2-(methoxycarbonylamino)-3,3-dimethylbutanoic acid-$d_9$ (XVII-$d_9$, $R^{1a}$=$R^{1b}$=$CH_3$, $R^2$=$R^3$=$C(CD_3)_3$; prepared according to Scheme 5). $^1$H-NMR (300 MHz, CDCl$_3$): δ 2.54 (d, 1H), 2.84-2.89 (m, 1H), 2.93 (d, 2H), 3.57 (d, 2H), 3.63 (s, 3H), 3.66 (s, 3H), 3.75 (d, 1H), 3.91-4.08 (m, 3H), 4.81 (bs, 1H), 5.15-5.32 (m, 2H), 6.36-6.45 (m, 2H), 7.18-7.24 (m, 6H, partially obscured by CDCl$_3$), 7.41 (d, 2H), 7.68-7.76 (m, 2H), 7.94 (d, 2H), 8,68 (d, 1H). HPLC (method: 20 min C18-RP column-gradient method 2-95% ACN+0.1% formic acid in 3.3 min with 1.7 min hold at 95% ACN; Wavelength: 254 nm): retention time: 3.23 min. MS (M+H$^+$): 723.6.

Example 3

Synthesis of 1,14-Di(methyl-d₃)(3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioate (Compound 103)

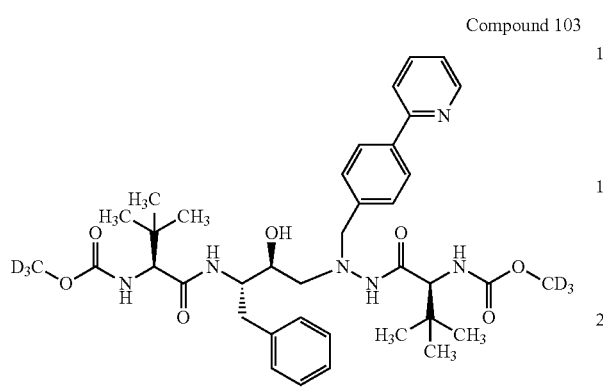

Compound 103

Compound 103 was prepared according to Scheme 1, above, following the General Method A described above.

Synthesis of 1,14-Di(methyl-d₃)(3S,8S,9S,12S)-3,12-bis(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioate (103). Compound 103 was prepared via General Method A, from (2S,3S)-3-amino-4-phenyl-1-(1-(4-(pyridin-2-yl)benzyl)hydrazinyl)butan-2-ol (XVI, $Y^{1a}=Y^{1b}=H$, hydrochloride) and known compound (S)-2-(methoxycarbonylamino)-3,3-dimethylbutanoic acid-d₃ (XVII-d₃, $R^{1a}=R^{1b}=CH_3$, $R^2=R^3=C(CD_3)_3$) (Zhang, Huiping et al., Journal of Labelled Compounds & Radiopharmaceuticals, 2005, 48(14), 1041-1047). ¹H-NMR (300 MHz, CDCl₃): δ 0.79 (s, 9H), 0.87 (s, 9H), 2.52 (d, 1H), 2.82-2.95 (m, 3H), 3.58 (d, 2H), 3.77 (d, 1H), 3.91-4.08 (m, 3H), 4.81 (s, 1H), 5.15-5.32 (m, 2H), 6.35-6.45 (m, 2H), 7.16-7.24 (m, 6H, partially obscured by CDCl₃), 7.41 (d, 2H), 7.68-7.76 (m, 2H), 7.94 (d, 2H), 8.68 (d, 1H). HPLC (method: 20 mm C18-RP column-gradient method 2-95% ACN+0.1% formic acid in 3.3 min with 1.7 min hold at 95% ACN; Wavelength: 254 nm): retention time: 3.24 min. MS (M+H⁺): 7.11.3.

Example 4

Synthesis of 1,14-Di(methyl-d₃)(3S,8S,9S,12S)-3,12-bis[(1,1-dimethylethyl)-d₉]-8-hydroxy-4,11-dioxo-9-(phenylmethyl)-6-[[4-(2-pyridinyl)phenyl]methyl-d₂]-2,5,6,10,13-pentaazatetradecanedioate (Compound 131)

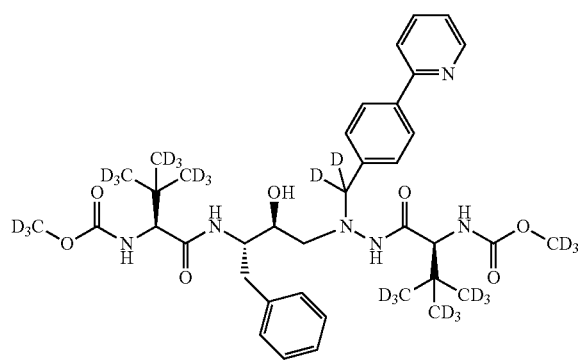

Compound 131

Compound 131 was prepared according to Scheme 1, above, following the General Method A described above. Deuterium gas (Cambridge Isotopes, 99.8 atom % D), MeOD (Aldrich, 99.5 atom % D), iPrOD (Aldrich, 98 atom % D) and deuterium chloride (Aldrich, 99 atom % D) were used in this synthesis. Deuterated aldehyde X was prepared according to Scheme 2b using LiAlD₄ (Cambridge Isotopes, 98 atom % D). ¹H-NMR (300 MHz, CDCl₃): δ 2.71 (dd, 2H), 2.94 (d, 2H), 3.56 (d, 2H), 3.77 (d, 1H), 4.02-4.05 (m, 1H), 4.83 (s, 1H), 5.19-5.29 (m, 2H), 6.40-6.47 (m, 2H), 7.20-7.23 (m, 6H, partially obscured by CDCl₃), 7.41 (d, 2H), 7.69-7.76 (m, 2H), 7.95 (d, 2H), 8.69 (d, 1H). HPLC (method: 20 mm C18-RP column-gradient method 2-95% ACN+0.1% formic acid in 3.3 min with 1.7 min hold at 95% ACN; Wavelength: 254 nm): retention time: 3.22 min; purity; 99.2%. MS (M+H⁺): 731.7.

Example 5

Synthesis of 1,14-Di(methyl-d₃)(3S,8S,9S,12S)-3-(1,1-dimethylethyl)-12-[(1,1-dimethylethyl)-d₉]-8-hydroxy-4,11-dioxo-9-(phenlymethyl)-6-[[4-(2-pyridinyl)phenyl]methyl]-2,5,6,10,13-pentaazatetradecanedioate (Compound 120)

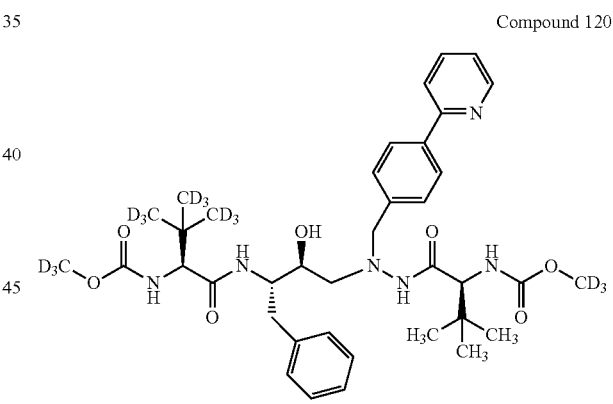

Compound 120

Compound 120 was prepared according to Scheme 1b, above. ¹H-NMR (300 MHz, CDCl₃): δ 0.78 (s, 9H), 2.72 (dd, 2H), 2.94 (d, 2H), 3.58-3.63 (m, 2H), 3.78 (d, 1H), 3.92-4.09 (m, 3H), 4.88 (s, 1H), 5.28 (dd, 2H), 6.46 (d, 1H), 6.73 (s, 1H), 7.14-7.25 (m, 6H, partially obscured by CDCl₃), 7.42 (d, 2H), 7.68-7.78 (m, 2H), 7.94 (d, 2H), 8.68 (d, 1H). HPLC (method: 20 mm C18-RP column-gradient method 2-95% ACN+0.1% formic acid in 3.3 min with 1.7 min hold at 95% ACN; Wavelength: 254 nm): retention time: 3.23 min; purity: 99.6%. MS (M+H⁺): 720.6.

Example 6

Synthesis of 1,14-Di(methyl-d₃)(3S,8S,9S,12S)-3-[(1,1-dimethylethyl)-d₉]-12-(1,1-dimethylethyl)-8-hydroxy-4,11-dioxo-9-(phenylmethyl)-6-[[4-(2-pyridinyl)phenyl]methyl]-2,5,6,10,13-pentaazatetradecanedioate (Compound 121)

Compound 121

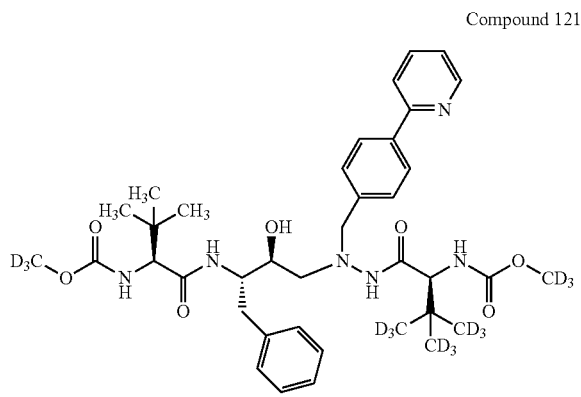

Compound 121 was prepared according to Scheme 1c, above. ¹H-NMR (300 MHz, CDCl₃): δ 0.86 (s, 9H), 2.72 (dd, 2H), 2.94 (d, 2H), 3.60-3.63 (m, 2H), 3.80 (d, 1H), 3.92-4.09 (m, 3H), 4.89 (s, 1H), 5.30 (dd, 2H), 6.43 (d, 1H), 6.74 (s, 1H), 7.14-7.26 (m, 6H, partially obscured by CDCl₃), 7.42 (d, 2H), 7.68-7.79 (m, 2H), 7.93 (d, 2H), 8.68 (d, 1H). HPLC (method: 20 mm C18-RP column-gradient method 2-95% ACN+0.1% formic acid in 3.3 min with 1.7 min hold at 95% ACN; Wavelength: 254 nm): retention time: 3.22 min; purity: 99.4%. MS (M+H⁺): 720.6.

Example 7

Synthesis of 1,14-Dimethyl(3S,8S,9S,12S)-3-(1,1-dimethylethyl)-12-[(1,1-dimethylethyl)-d₉]-8-hydroxy-4,11-dioxo-9-(phenylmethyl)-6-[[4-(2-pyridinyl)phenyl]methyl]-2,5,6,10,13-pentaazatetradecanedioate (Compound 104)

Compound 104

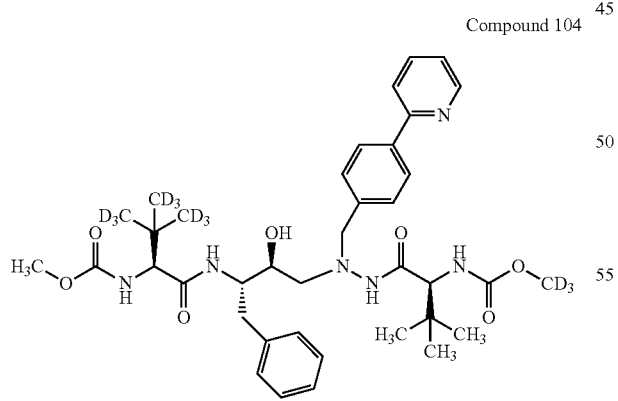

Compound 104 was prepared according to Scheme 1c, above. ¹H-NMR (300 MHz, CDCl₃): δ 0.78 (s, 9H), 2.70 (dd, 2H), 2.94 (d, 2H), 3.59-3.66 (m, 8H), 3.78 (d, 1H), 3.92-4.09 (m, 3H), 4.86 (s, 1H), 5.27 (dd, 2H), 6.44 (d, 1H), 6.63 (s, 1H), 7.14-7.26 (m, 6H, partially obscured by CDCl₃), 7.42 (d, 2H), 7.68-7.79 (m, 2H), 7.94 (d, 2H), 8.69 (d, 1H). HPLC (method: 20 mm C18-RP column-gradient method 2-95% ACN+0.1% formic acid in 3.3 min with 1.7 min hold at 95% ACN; Wavelength: 254 nm): retention time: 3.23 min; purity: 99.8%. MS (M+H⁺): 714.6.

Example 8

Synthesis of 1,14-Dimethyl(3S,8S,9S,12S)-3,12-bis[(1,1-dimethylethyl)-d₉]-8-hydroxy-4,11-dioxo-9-(phenylmethyl)-6-[[4-(2-pyridinyl)phenyl]methyl-d₂]-2,5,6,10,13-pentaazatetradecanedioate (Compound 113)

Compound 113

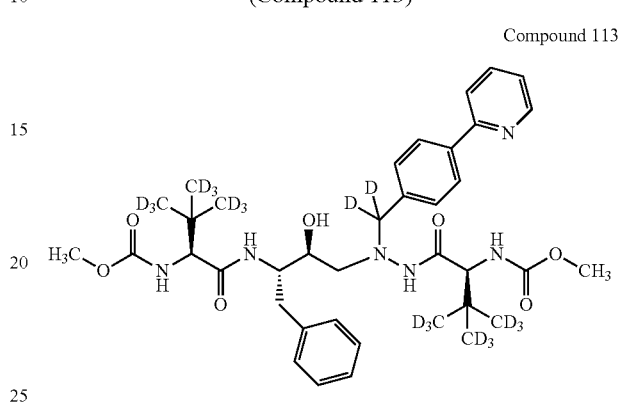

Compound 113 was prepared according to Scheme 1, above, following the General Method A described above. Deuterium gas (Cambridge Isotopes, 99.8 atom % D), MeOD (Aldrich, 99.5 atom % D), iPrOD (Aldrich, 98 atom % D) and deuterium chloride (Aldrich, 99 atom % D) were used in this synthesis. Deuterated aldehyde X was prepared according to Scheme 2b using LiAlD₄ (Cambridge Isotopes, 98 atom % D). ¹H-NMR (300 MHz, CDCl₃): δ 2.69 (dd, 2H), 2.94 (d, 2H), 3.56-3.59 (m, 2H), 3.64 (s, 3H), 3.67 (s, 3H), 3.77 (d, 1H), 4.02-4.05 (m, 1H), 4.84 (s, 1H), 5.18-5.32 (m, 2H), 6.40-6.45 (m, 2H), 7.14-7.26 (m, 6H, partially obscured by CDCl₃), 7.41 (d, 2H), 7.61-7.80 (m, 2H), 7.95 (d, 2H), 8.69 (d, 1H). HPLC (method: 20 mm C18-RP column-gradient method 2-95% ACN+0.1% formic acid in 3.3 min with 1.7 min hold at 95% ACN; Wavelength: 254 nm): retention time: 3.25 min; purity: 99.4%. MS (M+H⁺): 725.4.

Example 9

Synthesis of 1-Methyl-14-(methyl-d₃)(3S,8S,9S,12S)-3-(1,1-dimethylethyl)-12-[(1,1-dimethylethyl)-d₉]-8-hydroxy-4,11-dioxo-9-(phenylmethyl)-6-[[4-(2-pyridinyl)phenyl]methyl]-2,5,6,10,13-pentaazatetradecanedioate (Compound 114)

Compound 114

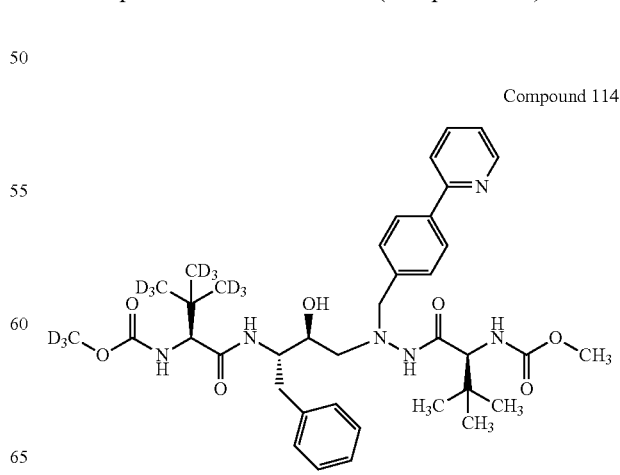

Compound 114 was prepared according to Scheme 1c above. Pd(OH)$_2$ was used in place of Pd/C for the conversion of XXXII to XXXIII. $^1$H-NMR (300 MHz, CDCl$_3$): δ 0.78 (s, 9H), 2.70 (dd, 2H), 2.93 (d, 2H), 3.59-3.63 (m, 5H), 3.78 (d, 1H), 3.92-4.04 (m, 3H), 4.84 (s, 1H), 5.30 (dd, 2H), 6.44 (d, 1H), 6.60 (s, 1H), 7.20-7.26 (m, 6H, partially obscured by CDCl$_3$), 7.41 (d, 2H), 7.70-7.79 (m, 2H), 7.94 (d, 2H), 8.68 (d, 1H). MS (M+H$^+$): 717.4.

Example 10

Synthesis of 1-Methyl-14-(methyl-d$_3$)(3S,8S,9S,12S)-3-(1,1-dimethylethyl)-12-[(1,1-dimethylethyl)-d$_9$]-8-hydroxy-4,11-dioxo-9-(phenylmethyl)-6-[[4-(2-pyridinyl)phenyl]methyl-$_2$]-2,5,6,10,13-pentaazatetradecanedioate (Compound 123)

Compound 123

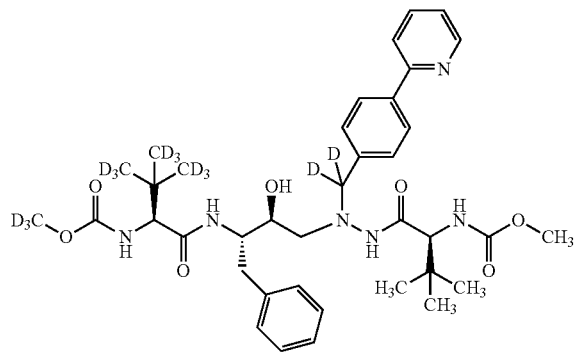

Compound 123 was prepared according to Scheme 1c above. Deuterium gas (Med-Tech, 98 atom % D), EtOD (Aldrich, 99.5 atom % D), MeOD (Aldrich, 99.5 atom % D), iPrOD (CDN, 99.1 atom % D) and deuterium chloride (Aldrich, 99 atom % D) were used in this synthesis. Pd(OH)$_2$ was used in place of Pd/C for the conversion of XXXII to XXXIII. $^1$H-NMR (300 MHz, CDCl$_3$): δ 0.79 (s, 9H), 2.72 (dd, 2H), 2.93 (d, 2H), 3.56-3.63 (m, 5H), 3.77 (d, 1H), 4.04 (d, 1H), 4.81 (s, 1H), 5.30 (dd, 2H), 6.41 (d, 1H), 6.51 (s, 1H), 7.14-7.26 (m, 6H, partially obscured by CDCl$_3$), 7.41 (d, 2H), 7.69-7.76 (m, 2H), 7.94 (d, 2H), 8.68 (d, 1H). MS (M+H$^+$): 719.5.

Example 11

Synthesis of 1,14-Dimethyl(3S,8S,9S,12S)-3-(1,1-dimethylethyl)-12-[(1,1-dimethylethyl)-d$_9$]-8-hydroxy-4,11-dioxo-9-(phenylmethyl)-6-[[4-(2-pyridinyl)phenyl]methyl-d$_2$]2,5,6,10,13-pentaazatetradecanedioate (Compound 111)

Compound 111

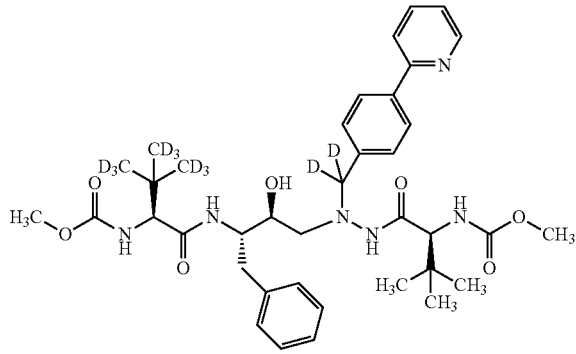

Compound 111 was prepared according to Scheme 1c above. Deuterium gas (Med-Tech, 98 atom % D), EtOD (Aldrich, 99.5 atom % D), MeOD (Aldrich, 99.5 atom % D), iPrOD (CDN, 99.1 atom % D) and deuterium chloride (Aldrich, 99 atom % D) were used in this synthesis. Pd(OH)$_2$ was used in place of Pd/C for the conversion of XXXII to XXXIII. $^1$H-NMR (300 MHz, CDCl$_3$): δ 0.79 (s, 9H), 2.74 (dd, 2H), 2.93 (d, 2H), 3.58-3.66 (m, 8H), 3.77 (d, 1H), 4.03 (d, 1H), 4.82 (s, 1H), 5.30 (dd, 2H), 6.41 (d, 1H), 6.51 (s, 1H), 7.20-7.26 (m, 6H, partially obscured by CDCl$_3$), 7.41 (d, 2H), 7.70-7.76 (m, 2H), 7.94 (d, 2H), 8.68 (d, 1H). MS (M+H$^+$): 716.5.

Example 12

Synthesis of 1,14-Di(methyl-d$_3$)(3S,8S,9S,12S)-3-(1,1-dimethylethyl)-12-[(1,1-dimethylethyl)-d$_9$]-8-hydroxy-4,11-dioxo-9-(phenylmethyl)-6-[[4-(2-pyridinyl)phenyl]methyl-d$_2$]-2,5,6,10,13-pentaazatetradecanedioate (Compound 129)

Compound 129

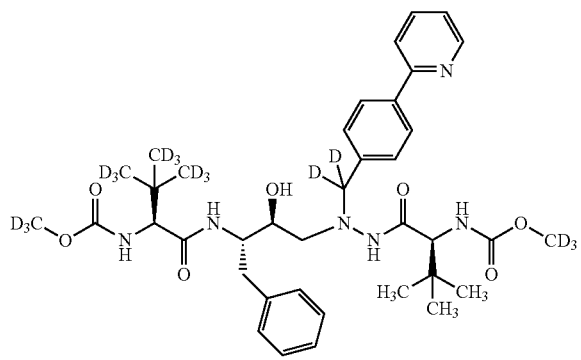

Compound 129 was prepared according to Scheme 1c above. Deuterium gas (Med-Tech, 98 atom % D), EtOD (Aldrich, 99.5 atom % D), MeOD (Aldrich, 99.5 atom % D), iPrOD (CDN, 99.1 atom % D) and deuterium chloride (Aldrich, 99 atom % D) were used in this synthesis. Pd(OH)$_2$ was used in place of Pd/C for the conversion of XXXII to XXXIII. $^1$H-NMR (300 MHz, CDCl$_3$): δ 0.79 (s, 9H), 2.71 (dd, 2H), 2.93 (d, 2H), 3.52-3.61 (m, 2H), 3.76 (d, 1H), 3.99-4.05 (m, 1H), 4.82 (s, 1H), 5.19-5.21 (m, 2H), 6.40-6.47 (m, 2H), 7.20-7.26 (m, 6H, partially obscured by CDCl$_3$), 7.42 (d, 2H), 7.69-7.76 (m, 2H), 7.95 (d, 2H), 8.69 (d, 1H). MS (M+H$^+$): 722.5.

Example 13

Synthesis of (S)-2-(d$_3$-methoxy-carbonylamino)-3,3-d$_9$-dimethylbutanoic Acid (XVII-d$_{12}$) Intermediate XVII-d$_{12}$ (R$^2$=R$^3$=C(CD$_3$)$_3$; R$^{1a}$=R$^{1b}$=CD$_3$ was prepared according to Scheme 5, above. Details of the synthesis are set forth below.

Synthesis of d$_9$-pivalaldehyde (XXII, R$^2$=R$^3$=C(CD$_3$)$_3$). In a 3-L 4-necked round bottom flask fitted with mechanical stirrer, reflux condenser, dropping funnel and thermometer were placed a few small crystals of iodine and then magnesium turnings (24.7 g, 1.029 mol). The bottom of the flask was heated with a heat gun until the iodine commenced to vaporize and was then allowed to cool while a solution of t-butyl chloride-$d_9$ (100.0 g, 1.029 mol, Cambridge Isotopes, 99 atom % D) in anhydrous ether was placed in the dropping funnel. A solution of t-butyl chloride-$d_9$ in ether (3-5 mL) was added directly to the dry magnesium. More anhydrous ether (1 L) and a few small crystals of iodine were added, and the resulting mixture was heated for 0.5 hr to initiate the reaction. The rest of solution of t-butyl chloride-$d_9$ in ether was added with stirring at a rate not faster than one drop per second. The mixture was allowed to reflux during the halide-ether addition and no external cooling was applied. The reaction mixture was then heated at reflux for several hours until almost all of magnesium disappeared. The mixture was cooled to −20° C., and a solution of anhydrous DMF (73.0 g, 1.0 mol) in ether (100 mL) was added over a 35 min period at such a rate that the temperature of the reaction did not exceed −15° C. A second solution of anhydrous DMF (73.0 g, 1.0 mol) was then added quickly at −8° C. After an additional 5 min, hydroquinone (0.5 g) was added, stirring was stopped, the cooling bath was removed, and the mixture was left standing overnight at ambient temperature under nitrogen. The mixture was cooled to 5° C. and aqueous 4M HCl (600 mL) was added in portions to quench the reaction. The mixture was diluted with water (400 mL), and the layers were separated. The aqueous layer was extracted with ether (3×200 mL), and the combined organic layers were dried and filtered. The filtrate was subjected to fractional distillation under atmosphere pressure of nitrogen to remove most of the ether. The residue was transferred to a small flask and fractional distillation was continued to collect the desired compound XXII ($R^2=R^3=C(CD_3)_3$) (39.5 g, 40% yield) as a colorless oil at 65-75° C. Compound XXII ($R^2=R^3=C(CD_3)_3$) was stored under nitrogen in the freezer.

Synthesis of (R)-2-((S)-1-cyano-2,2-$d_9$-dimethylpropylamino)-2-phenylacetamide (XXIIa, $R^2=R^3=C(CD_3)_3$). To a stirred suspension of (R)-phenylglycine amide (60.7 g, 400 mmol) in water (400 mL) was added Compound XXII ($R^2=R^3=C(CD_3)_3$) (39.5 g, 415 mmol) at room temperature (rt). Simultaneously, 30% aqueous NaCN solution (68.8 g, 420 mmol) and glacial acetic acid (25.4 g, 423 mmol) were added in 30 min, whereby the temperature of the reaction increased to 34° C. The mixture was stirred for 2 hrs at 30° C., followed by stirring at 70° C. for 20 hrs. After cooling to 30° C., the product was isolated by filtration. The solid was washed with water (500 mL) and dried under vacuum at 50° C. to afford the desired compound XXIIa ($R^2=R^3=C(CD_3)_3$) (90.0 g, 88% yield) as a tan solid with $[\alpha]_D=-298°$ (c=1.0, CHCl$_3$).

Synthesis of (S)-2-((R)-2-amino-2-oxo-1-phenylethylamino)-3,3-$d_9$-dimethylbutanamide (XXIIb, $R^{2/3}=C(CD_3)_3$). A solution of compound XXIIa ($R^2=R^3=C(CD_3)_3$) (64.2 g, 252.4 mmol) in dichloromethane (500 mL) was added to concentrated. sulfuric acid (96%, 350 mL) at 15-20° C. through an addition funnel under the cooling of an ice bath. The resulting mixture was stirred at room temperature (rt) for 1 hr. The mixture was poured onto ice and carefully neutralized by NH$_4$OH solution to pH=9. The mixture was extracted with dichloromethane and the combined organic layers were washed with water, dried, filtered, and concentrated in vacuo to afford the desired compound XXIIb ($R^2=R^3=C(CD_3)_3$) (55.0 g, 80% yield) as a yellow foam with $[\alpha]_D=-140°$ (c=1.0, CHCl$_3$).

Synthesis of (S)-2-amino-3,3-$d_9$-dimethylbutanamide (XXIIc, $R^{2/3}=C(CD_3)_3$). A mixture of compound XXIIb ($R^2=R^3=C(CD_3)_3$) (77.0 g, 282.7 mmol), 10% Pd/C (~50% water, 20 g) and acetic acid (50 mL) in ethanol (1.2 L) was subjected to hydrogenation at 30 psi at rt for several days until LCMS showed that the reaction was complete. The mixture was filtered through Celite and washed with EtOAc. After the filtrate was concentrated in vacuo, the residue was diluted with water (1 L) and basified with 1M NaOH solution to pH=9. The mixture was extracted with dichloromethane and the aqueous layer was concentrated in vacuo to half volume, saturated with solid NaCl, and extracted with THF. The combined extracts were dried, filtered, and concentrated in vacuo. The residue was chased with toluene to remove remaining water, followed by trituration with dichloromethane to afford the desired compound XXIIc ($R^2=R^3=C(CD_3)_3$) (38.0 g, 96% yield) as a white solid.

Synthesis of (S)-2-amino-3,3-$d_9$-dimethylbutanoic acid hydrochloride (XXV, $R^{2/3}=C(CD_3)_3$). A mixture of compound XXIIc ($R^2=R^3=C(CD_3)_3$) (31.0 g, 222.6 mmol) in 6M aqueous HCl solution (1.5 L) was heated at reflux for 24 hrs. The mixture was concentrated in vacuo to give the crude product. The solid was redissolved in water (500 mL) and washed with EtOAc (2×200 mL) to remove impurities from previous steps. The aqueous layer was then concentrated in vacuo, chased with toluene, and dried under vacuum at 50° C. to afford the HCl salt of the desired compound (S)-2-amino-3,3-dimethylbutanoic acid-$d_9$ hydrochloride (XXV, $R^2=R^3=C(CD_3)_3$) (33.6 g, 85% yield) as a white solid.

Synthesis of (S)-2-($d_3$-methoxycarbonylamino)-3,3-$d_9$-dimethylbutanoic acid (XVII-$d_{12}$). To a solution of compound XXV ($R^2=R^3=C(CD_3)_3$) (4.42 g, 25.0 mmol) in a mixture of dioxane (12.5 mL) and 2M NaOH solution (60 mL) was added methyl chloroformate-$d_3$ (5.0 g, 50.0 mmol, Cambridge Isotopes, 99 atom % D) dropwise, keeping the internal temperature below 50° C. The resulting mixture was warmed to 60° C. and stirred overnight, and then cooled to rt. The mixture was washed with dichloromethane and the aqueous layer was acidified with conc. HCl to pH=2 and extracted with EtOAc. The combined extracts were dried, filtered, and concentrated in vacuo to afford the desired compound (S)-2-(methoxycarbonylamino)-3,3-dimethylbutanoic acid-$d_{12}$ (XVII-$d_{12}$) (3.8 g) as a yellow oil.

Example 14

Synthesis of (S)-2-(methoxycarbonylamino)-3,3-$d_9$-dimethylbutanoic Acid (XVII-$d_9$)

Intermediate XVII-$d_9$ ($R^2=R^3=C(CD_3)_3$; $R^{1a}=R^{1b}=CH_3$) was prepared following Scheme 5 and the method described above for the synthesis of XVII-$d_{12}$, substituting methyl chloroformate for methyl chloroformate-$d_3$ in the final step.

Example 15

(S)-2-($d_3$-methoxycarbonylamino)-3,3-dimethylbutanoic Acid (XVII-$d_3$)

Intermediate XVII-$d_3$ ($R^2=R^3=C(CH_3)_3$; $R^{1a}=R^{1b}=CD_3$) is known in the literature (Zhang, H et al, J Label Comp Radiopharm 2005, 48(14):1041-1047) and was prepared from methyl chloroformate-$d_3$ (Cambridge Isotopes, 99 atom % D).

Example 16

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al,, Pharm Res, 1997, 14:152, Microsomal Assay. Human liver microsomes (20 mg/mL, pool of 50 individuals) were obtained from Xenotech LLC (Lenexa, Kans.). The incubation mixtures are prepared as follows. Stock solutions (10 mM) solutions of test Compounds 103, 106, 122 and of atazanavir were prepared in DMSO. The 10 mM stock solutions were diluted to 1 mM in acetonitrile (ACN). The 20 mg/mL liver microsomes were diluted to 0.625 mg/mL in 0.1 M potassium phosphate buffer, pH 7.4, containing 3 mM $MgCl_2$. 1 mM test compound was added to the diluted microsomes to obtain a mixture containing 1.25 µM test compound. The microsome-test compound mixtures were added to wells of a 2 mL 96-well deep well polypropylene plate in triplicate. The plate was warmed to 37° C. before initiating the reactions by addition of pre-warmed NADPH in 0.1 M potassium phosphate buffer, pH 7.4, containing 3 mM $MgCl_2$. The final reaction mixture composition contained:

Liver Microsomes 0.5 mg/mL

NADPH 2 mM

Potassium Phosphate, pH 7.4 100 mM

Magnesium Chloride 3 mM

Test Compound 1.0 µM.

The reaction mixtures were incubated at 37° C. and 50 µL aliquots were removed at 0, 3, 7, 12, 20, and 30 minutes and added to shallow-well 96-well plates which contained 50 µL of ice-cold ACN with internal standard to stop the reactions. The plates were stored at −20° C. for 30 minutes, after which 100 µL of water was added to the wells of the plate before centrifugation to pellet precipitated proteins. Supernatants were transferred to another 96-well plate and analyzed for amounts of parent remaining by LC-MS/MS using an Applied Biosystems API 4000 mass spectrometer.

The in vitro $t_{1/2}$s for test compounds were calculated from the slopes of the linear regression of % parent remaining (ln) vs incubation time relationship using the formula: in vitro $t_{1/2}$=0.693/k, where k=−[slope of linear regression of % parent remaining(ln) vs incubation time]. Data analysis was performed using Microsoft Excel Software.

The results are shown in FIG. 1 and in Table 2 below.

TABLE 2

Stability of Tested Compounds in Human Liver Microsomes

| Compound | $T_{1/2}$ ± SD |
|---|---|
| 103 | 20.19 ± 4.22 |
| 106 | 26.13 ± 0.99 |
| 122 | 35.39 ± 1.68 |
| atazanavir | 18.63 ± 2.99 |

Under the assay conditions tested compounds 103, 106 and 122 all demonstrated an increased half-life as compared to atazanavir. Compounds 106 and 122 showed the greatest differentiation as compared to atazanavir, demonstrating an approximately 40% and 67% increase in half-life, respectively.

Figure 2:
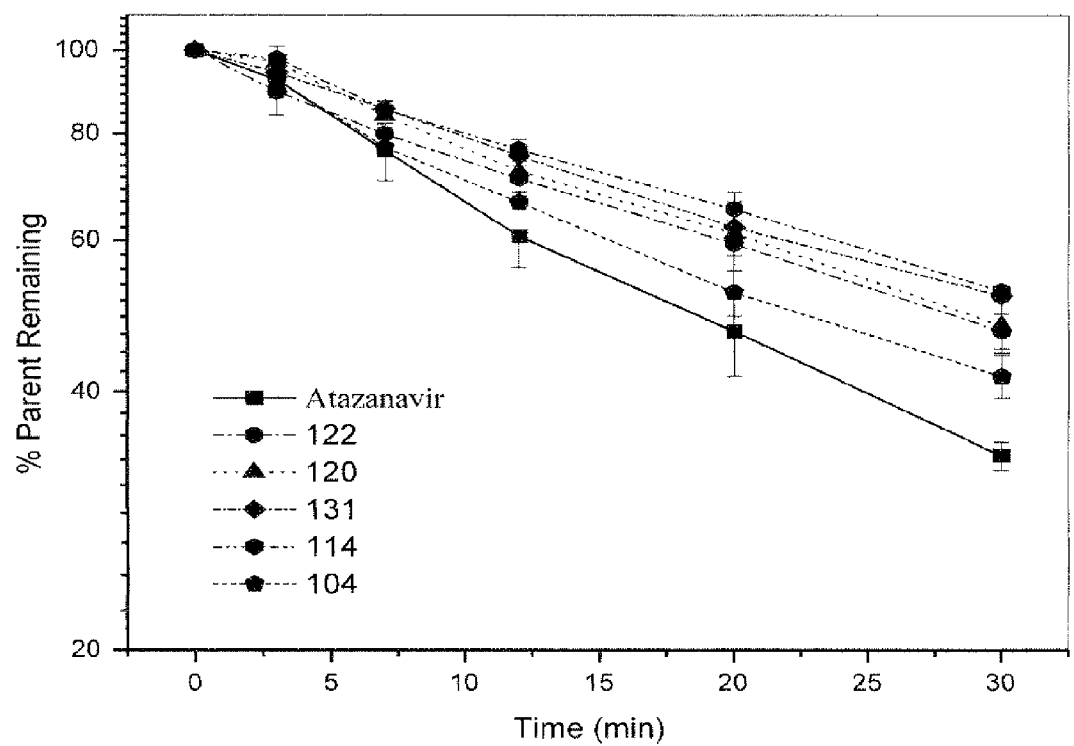
FIG. 2 is a graph showing the relative stability of compounds of this invention in human liver microsomes as compared to atazanavir.
Figure 3:
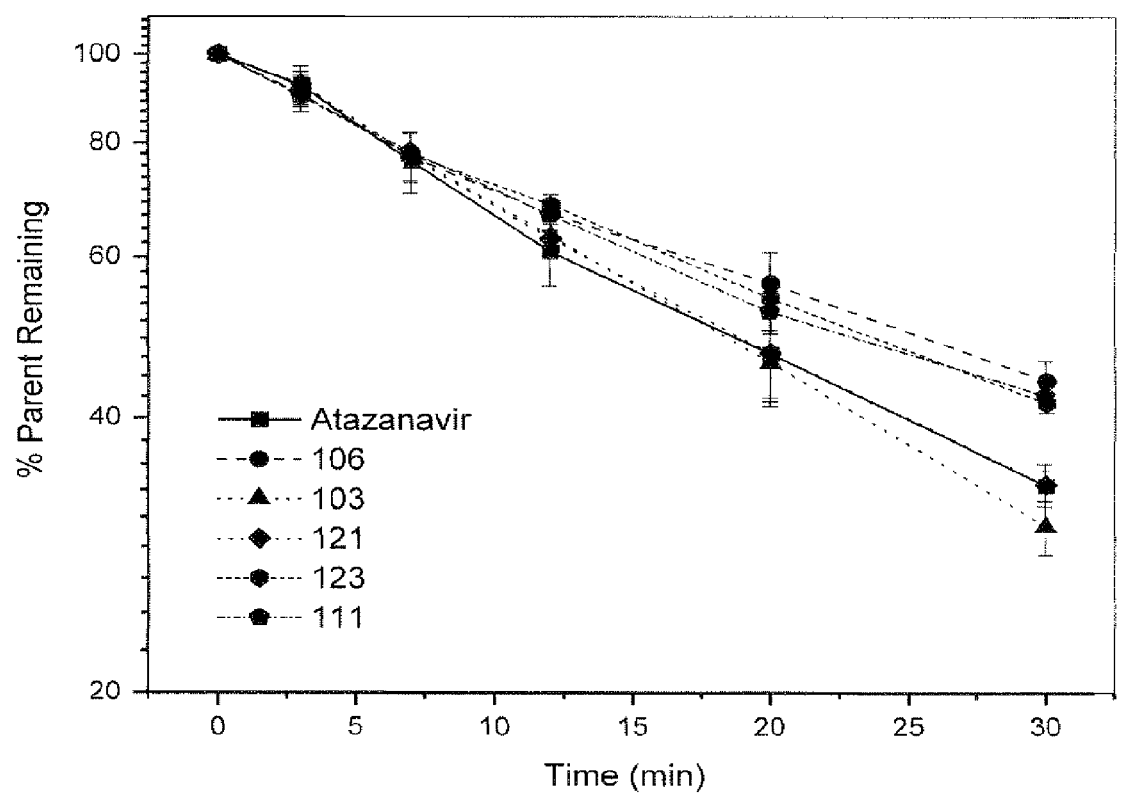
FIG. 3 is a graph showing the relative stability of compounds of this invention in human liver microsomes as compared to atazanavir.

The above-described assay was repeated using atazanavir and Compounds 103, 104, 106, 111, 114, 120, 121, 122, 123 and 131. The results are shown in FIGS. 2 and 3 and in Table 3, below:

TABLE 3

Stability of Tested Compounds in Human Liver Microsomes

| Compound | $t_{1/2}$ (min) Avg ± SD (n = 3) | % change in $t_{1/2}$ |
|---|---|---|
| atazanavir | 18.8 ± 0.6 | – |
| 106 | 25.6 ± 0.6 | +36 |
| 103 | 17.2 ± 0.9 | −9 |
| 122 | 28.3 ± 0.3 | +51 |
| 120 | 26.9 ± 1.4 | +43 |
| 121 | 18.8 ± 1.5 | — |
| 131 | 30.9 ± 1.4 | +64 |
| 104 | 23.3 ± 0.4 | +24 |
| 114 | 31.5 ± 0.8 | +68 |
| 123 | 23.9 ± 0.8 | +27 |
| 111 | 23.9 ± 0.3 | +27 |

Under the assay conditions, compounds 104, 106, 111, 114, 120, 122, 123 and 131 all demonstrated an increased half-life of ≧24% compared to atazanavir.

Example 17

Pharmacokinetic Properties

The pharmacokinetic properties of the compounds of the invention were tested in both rats and chimpanzees using both oral and intravenous dosing.

Rat Pharmacokinetics. Compound 122 and atazanavir were dissolved in a 5% glucose solution with 10% DMI, 15% EtOH and 35% PG respectively up to 2 mg/mL. Then the combo dose was prepared by mixing both by 1:1 to yield a final concentrations at 1 mg/mL for each compound (pH=5-6) for intravenous and oral administration.

Male Sprague-Dawley rats (body weight: 170 g to 235 g) were used in this study. Rats were dosed either orally or intravenously with either Compound 122 (2 mg/kg), atazanavir (2 mg/kg) or a 1:1 combination of Compound 122 and atazanavir (1 mg/kg of each). Blood samples (300 µL) were collected via the retro-orbital vein at pre-dose and 0.083, 0.25, 0.5, 1, 2, 4, 6, 8, 10, 12 and 24 hours post-dose. Blood samples were placed into heparinized eppendorf tubes (evaporated) and then centrifuged at 8000 rpm for 6 minutes. 100 µL aliquots of plasma were transferred to clean Eppendorf tubes and stored with the dose formulation at −20° C. until bioanalysis. For bioanalysis, plasma was thawed and added to it was 20 µL methanol and 500 µL of a 50 ng/ml internal standard solution (quetiapine in methanol). The sample was vortexed, centrifuged at 15,000 rpm for 5 minutes and the supernatant transferred to glass autosampler vials.

Analyses of plasma samples were performed using a high performance liquid chromatography/mass spectrometry (HPLC/MS/MS) method. The LC system comprised an Agilent (Agilent Technologies Inc, USA) liquid chromatograph equipped with an isocratic pump (1100 series), an autosampler (1100 series) and a degasser (1100 series). Mass spectrometric analysis was performed using an API3000 (triple-quadrupole) instrument from AB Inc (Canada) with an ESI interface. The data acquisition and control system were created using Analyst 1.4 software from ABI Inc. Following intravenous co-administration of Compound 122 and atazanavir, atazanavir disappeared more rapidly from the blood. The accelerated reduction of atazanavir as compared to Compound 122 began between 1 and 2 hours post-IV administration.

The half-life and AUC following intravenous injection are shown in the table 4 below. Compound 122 showed a 10.7% increase in half-life and a 6.0% increase in AUC following intravenous injection.

TABLE 4

Half-life of Compound 122 versus Atazanavir Following Intravenous Co-Dosing in Rats.

| Compound | $T_{1/2}$ (h) | AUC (ng*h/mL) |
|---|---|---|
| Atazanavir | 0.23 ± 0.01 | 475 ± 15.9 |
| 122 | 0.25 ± 0.02 | 503 ± 25.1 |

Oral co-administration of Compound 122 and atazanavir produced an even more pronounced difference in pharmacokinetics between the two compounds. As shown in Table 5, Compound 122 demonstrated a significant increase in $C_{max}$ as compared to atazanavir following oral co-dosing. The $C_{max}$, half-life and AUC of the two compounds following oral co-administration is shown in the table below. Compound 122 showed a 43% increase in half-life, a 67% increase in $C_{max}$, and an 81% increase in AUC as compared to atazanavir after oral co-dosing of the two compounds in rats.

TABLE 5

Half-life, $C_{max}$, $C_{min}$. and AUC of Compound 122 versus Atazanavir Following Oral Co-Dosing in Rats.

| Compound | $T_{1/2}$ (h) | $C_{max}$ (ng/mL) | AUC (ng*h/mL) |
|---|---|---|---|
| Atazanavir | 0.32 ± 0.06 | 109 ± 67.2 | 86 ± 51.2 |
| 122 | 0.46 ± 0.16 | 183 ± 113.2 | 156 ± 70.6 |

Chimp Pharmacokineties. Run A: A 4 mg/mL solution of atazanavir and each of Compounds 114, 120 and 122 were prepared in 10% DMI (dimethyl isosorbide), 15% EtOH, 35% PG in D5W. Specifically, for each compound, 240 mgs of compound was dissolved in a solution composed of 6 mL of DMI, 9 mL of EtOH and 21 mL PG. Once the compound was fully dissolved, 24 mL of D5W was added and the solution mixed. This resulted in a 60 mL solution at 4 mg/mL for each compound.

Fifty-five mL of each drug solution is then combined and the mixture was sterile filtered using a 0.2 μm filter. This produced 220 mL of a 1:1:1:1 mixture atazanavir:Compound 114:Compound 120:Compound 122. The final concentration of each drug in the solution was 1 mg/mL. Each animal received 50 mL of this solution through either IV or PO routes.

Four chimps (two male and two female) were used in this study and were fasted overnight prior to administration of the compound solution. Animals were sedated with ketamine and/or telazol prior to dosing. Intravenous dosing was achieved by IV infusion over 30 minutes.

Figure 4:
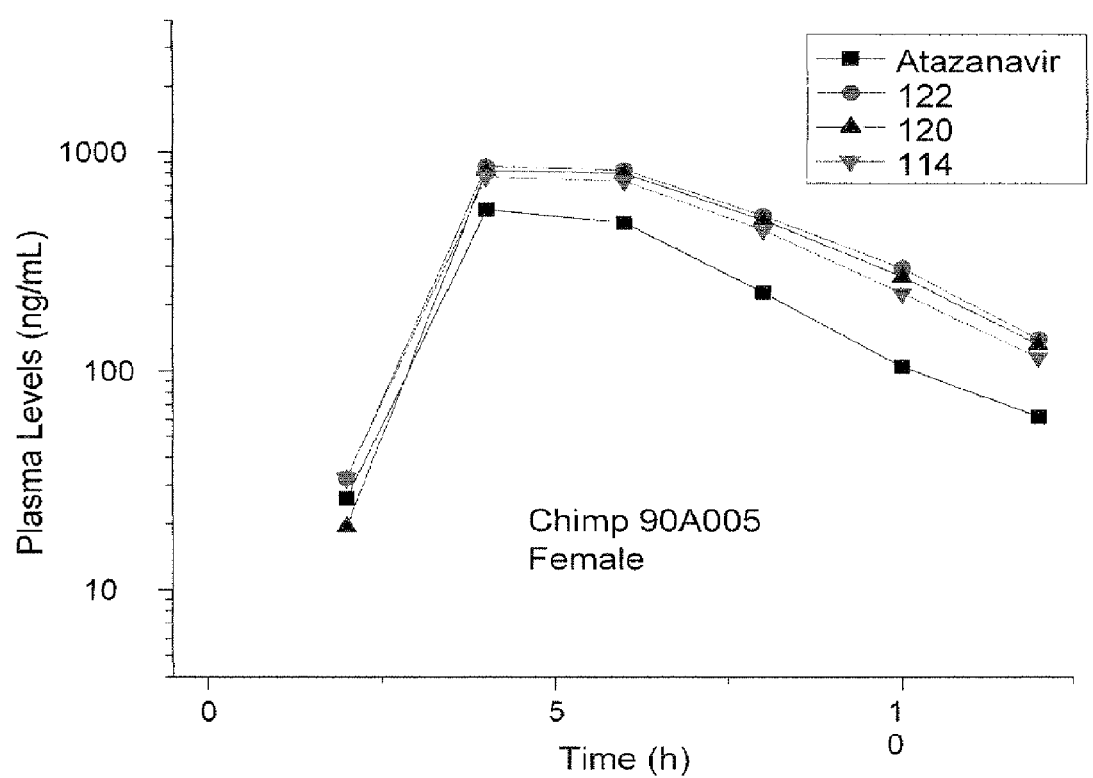
FIG. 4 is a graph showing the relative plasma levels of compounds of this invention following oral administration to chimps as compared to atazanavir.
Figure 5:
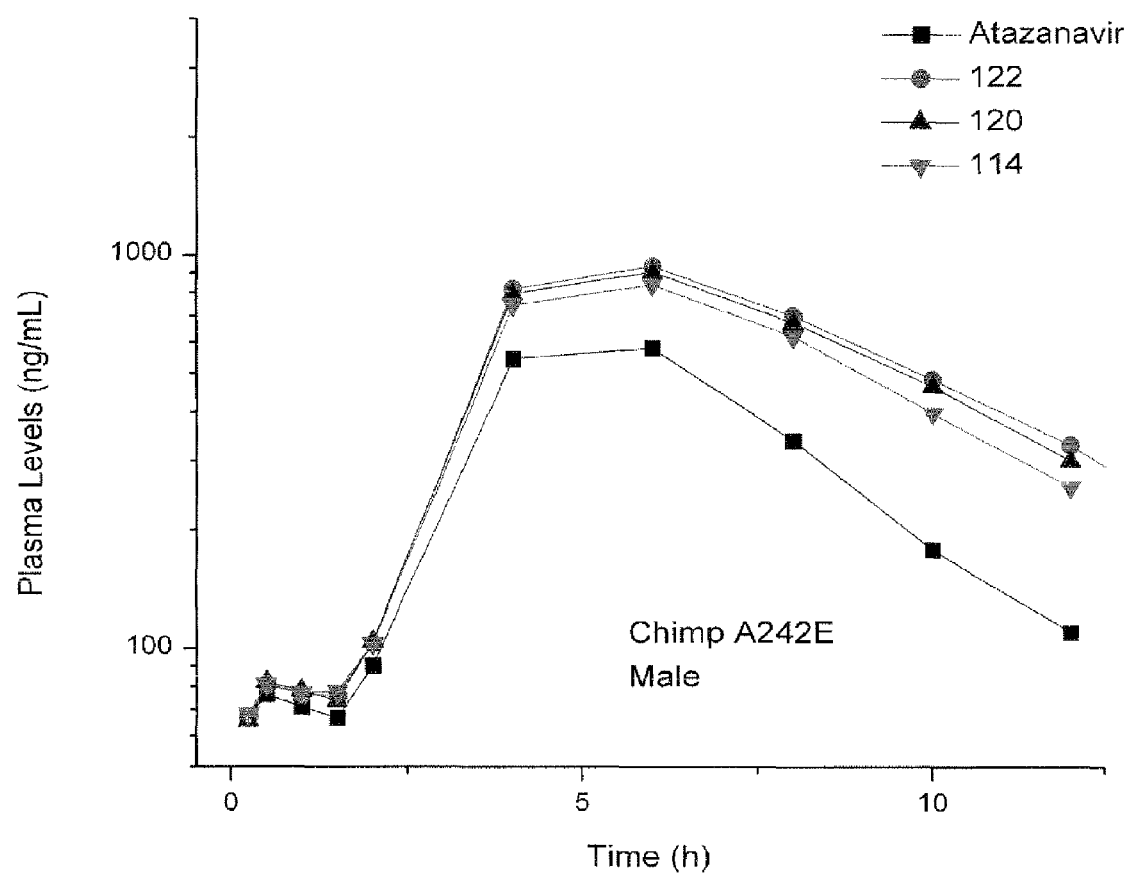
FIG. 5 is a graph showing the relative plasma levels of compounds of this invention following oral administration to chimps as compared to atazanavir.

Approximately 4.5 mL of blood was collected into vacutainer tubes with sodium heparin as an anticoagulant at 0 (preinfusion), 15 min., 29.5 min (immediately before the end of the infusion), and then at 6, 15, 30, and 45 minutes, and 1, 2, 4, 6, 8, 10, 12, 24 hours after the infusion is stopped. A similar procedure was used to collect blood after oral dosing with samples taken at 0 (predose), 15, and 30 minutes, and at 1, 1.5, 2, 4, 6, 8, 10, 12, 24 hours postdose. Following sample collection, the vacutainer tubes were rocked by hand several times to insure adequate mixing. Blood samples were placed immediately on wet ice and centrifuged within 1 hour from time of collection. Following centrifugation, the resulting plasma was stored frozen at −70° C. until analysis. The results are summarized in FIGS. 4 and 5 and tables 6 and 7.

The percentage increase in half-life of the compounds of this invention relative to atazanavir following intravenous co-administration is shown in Table 6 below. Compounds 120, 122, and 114 had significantly longer half lives than atazanavir when co-dosed in chimps.

TABLE 6

Percent Increase in Half-Life Relative to Atazanavir Following Intravenous Co-Dosing in Chimps.

| Compound | Female Chimp $T_{1/2}$ % Over Atazanavir | Male Chimp $T_{1/2}$ % Over Atazanavir |
|---|---|---|
| 122 | 44% | 60% |
| 120 | 42% | 58% |
| 114 | 32% | 46% |

Concentrations in ng/mL of compounds 120, 122, and 114 detected intact in urine 24 hours after intravenous or oral administration are summarized in Table 7. Table 7 also shows the ratio of each tested compound of this invention as compared to atazanavir. There were higher concentrations of the unmetabolized tested compounds in the urine as compared to atazanavir, indicating a slower rate of metabolism for the tested compounds as compared to atazanavir.

TABLE 7

Higher Urine Concentrations of Tested Compounds Compared to Atazanavir in Co-Dosed Chimps.

| | | Compound Tested | | | | Ratios 122: Atazanavir | Ratios 120: Atazanavir | Ratios 114: Atazanavir |
|---|---|---|---|---|---|---|---|---|
| CHIMP | Admin | Atazanavir | 122 | 120 | 114 | | | |
| 90A005 | PO | 516 | 1180 | 1110 | 963 | 2.29 | 2.15 | 1.8 |
| A242E | | 569 | 1280 | 1230 | 1070 | 2.25 | 2.16 | 1.8 |
| A207B | IV | 2000 | 3130 | 3030 | 2750 | 1.57 | 1.52 | 1.3 |
| A336C | | 1790 | 3250 | 3110 | 2820 | 1.82 | 1.74 | 1.5 |

Run B: Same as Run A, except the dose was 150 mg orally of each of atazanavir and compounds 114 and 120, and the vehicle was 10 percent ethanol, 40 percent polypropylglycol in 2.5 percent citric acid. The $C_{max}$, $C_{min}$, half-life, AUC, and clearance (CL, mL/minute/kg) of the compounds following oral co-administration are shown in table 8 and 9 below and FIGS. 4 and 5. Compounds 114 and 120 had significantly longer half lives $C_{max}$, $C_{min}$, and AUC, and had slower clearance rates than atazanavir when co-dosed in chimps.

TABLE 8

Run B: $T_{1/2}$, $C_{max}$, $C_{min}$. AUC, and Clearance Differences of Tested Compounds Following Oral Co-Dosing in Chimps.

| Compound | $T_{1/2}$ | $C_{max}$ | $C_{min}$ | $AUC_{0-12}$ | CL |
|---|---|---|---|---|---|
| Atazanavir | 4.1 | 2800 | 32 | 19560 | 96 |
| 120 | 6.5 | 3590 | 69 | 26930 | 65 |
| 114 | 6.2 | 3180 | 48 | 23890 | 73 |

Concentrations in ng/mL of the administered compounds detected intact in urine 24 hours after oral administration are summarized in Table 9. There were higher concentrations of the unmetabolized compound 120 and 114 in the urine as compared to atazanavir, indicating a slower rate of metabolism for the tested compounds.

TABLE 9

Run B: Higher Urine Concentrations of Tested Compounds
Compared to Atazanavir in Co-Dosed Chimps.

| CHIMP | Admin | Compound | | | Ratios | |
|---|---|---|---|---|---|---|
| | | Atazanavir | 120 | 114 | 120: Atazanavir | 114: Atazanavir |
| 91A005 | PO | 1640 | 2930 | 2530 | 1.79 | 1.54 |
| 96A021 | | 3260 | 5030 | 4580 | 1.54 | 1.40 |

Example 18

HIV Anti-Viral Activity

The HIV antiviral activity of compound of the present invention was tested in CEM-SS cells infected with HIV-1. CEM-SS cells were passaged in T-75 flasks in RPMI 1640 medium supplemented with 10% heat inactivated fetal bovine serum, 2 mmol/L L-glutamine, 100 U/mL penicillin and 100 flg/mL streptomycin prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $5\times10^4$ cells per mL in tissue culture medium and added to the drug-containing microtiter plates in a volume of 50 μL.

The virus used for the assay was the lymphocyte-tropic virus strain HIV-$1_{RF}$. The virus was obtained from the NIH AIDS Research and Reference Reagent Program and stock virus pools were produced in CEM-SS cells. A pre-titered aliquot of virus was removed from the freezer (–80° C.) and allowed to thaw slowly to room temperature in a biological safety cabinet. Virus was resuspended and diluted into tissue culture medium such that the amount of virus added to each well in a volume of 50 μL was the amount determined to yield 85 to 95% cell killing at 6 days post-infection.

Each plate contains cell control wells (cells only), virus control wells (cells plus virus), compound toxicity wells (cells plus compound only), compound colorimetric control wells (compound only) as well as experimental wells (compound plus cells plus virus). Samples were tested in triplicate with eleven half-log dilutions per compound starting at 0.1 μM of compound. Compounds 104, 120 and 122 were tested, as was atazanavir and AZT. All compounds were also tested in the presence of 2 mg/mL $\alpha_1$ acid glycoprotein (AAGP), 10 mg/mL human serum albumin (HSA) or a combination of AAGP plus HAS.

Following incubation at 37° C. in a 5% $CO_2$ incubator, the test plates were stained with the tetrazolium dye XTT (2,3-bis(2-methoxy-4-nitro-5sulfophenyl)-5-[(phenylamino)carbonyl]-2H-tetrazolium hydroxide). XTT-tetrazolium was metabolized by the mitochondrial enzymes of metabolically active cells to a soluble formazan product, allowing rapid quantitative analysis of the inhibition of HIV induced cell killing by anti-HIV test substances. XTT solution was prepared daily as a stock of 1 mg/mL in RPMI 1640. Phenazine methosulfate (PMS) solution was prepared at 0.15 mg/mL in PBS and stored in the dark at –20° C. XTT/PMS stock was prepared immediately before use by adding 40 μL of PMS per mL of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Raw data was collected from the Softmax Pro 4.6 software and imported into a Microsoft Excel 2003 spreadsheet for analysis by linear curve fit calculations. The results of the assay are shown in the table 10 below.

TABLE 10

HIV Anti-viral Activity in CEM-SS cells infected with HIV-1

| | CEM-SS/HIV-$1_{RF}$ $EC_{50}$ (nM) | | | |
|---|---|---|---|---|
| Compound | No Serum Protein Added | +0.5 mg/mL AAGP | +10 mg/mL HAS | +AAGP + HSA |
| AZT | 2 | 1 | 2 | 2 |
| Atazanavir | 1 | 4 | 4 | 8 |
| 104 | <0.3 | 2 | 0.9 | 4 |
| 120 | 0.5 | 3 | 1 | 4 |
| 122 | 0.4 | 2 | 0.8 | 6 |

Compounds 122 and 120 yielded $EC_{50}$ values of less than 0.4 and 0.5 nM, respectively, in cell culture medium and a 5 to 6-fold increase to 2 and 3 nM, respectively, in the presence of 0.5 mg/mL AAGP. Compound 104 yielded an $EC_{50}$ value of less than 0.3 nM in cell culture medium and a greater than 7-fold increase to 2 nM in the presence of AAGP. In the presence of 10 mg/mL HSA, Compounds 104, 120 and 122 yielded $EC_{50}$ values of 0.8, 1 and 0.9 nM, respectively, which was two- to greater than three-fold less potent than in cell culture medium alone. Antiviral activity decreased 8 to 15-fold for compound 122 and 120 in the presence of AAGP plus HSA with $EC_{50}$ values of 6 and 4 nM, respectively. Compound 104 yielded an $EC_{50}$ value of 4 nM in the presence of AAGP plus HSA, which was greater than 13-fold less potent than in cell culture medium alone. The presence of AAGP, alone or in combination with HSA, resulted in the most significant protein binding and loss of antiviral activity for Compounds 104, 120 and 122. Each of these serum protein affects is simlar to that observed for atazanavir. Each of the compounds of this invention tested in this assay were at least as potent as atazanavir.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of the following formula

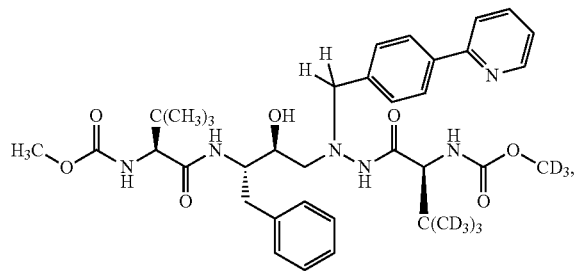

or a pharmaceutically acceptable salt thereof, wherein any atom not designated as deuterium is present at its natural isotopic abundance.

2. A pharmaceutical composition comprising the compound claim 1 and a pharmaceutically acceptable carrier.

3. The composition of claim 2, additionally comprising a second therapeutic agent selected from a second HIV protease inhibitor, a non-nucleoside reverse transcriptase inhibitor, a nucleoside/nucleotide reverse transcriptase inhibitor, a viral entry inhibitor, an integrase inhibitor, an immune based antiretroviral agent, a viral maturation inhibitor, a cellular inhibitor, or combinations of two or more of the above.

4. The composition of claim 3, wherein the second therapeutic agent is selected from ritonavir, efavirenz, didanosine, tenofovir disoproxil, nelfinavir mesilate, aniprenavir, raltegravir potassium, saquinavir, lopinavir, nevirapine, emtricitabine, abacavir, lamivudine, zidovudine, maraviroc, stavudine, darunavir, fosamprenavir, vicriviroc, a pharmaceutically acceptable salt of any of the foregoing, and combinations thereof.

5. The composition of claim 4, wherein the second therapeutic agent is selected from ritonavir, efavirenz, didanosine, raltegravir potassium, tenofovir disoproxil, lamivudine, abacavir, zidovudine, emtricitabine, a pharmaceutically acceptable salt of any of the foregoing, and combinations thereof.

6. The composition of claim 5, comprising two to three additional second therapeutic agents independently selected from ritonavir, efavirenz, didanosine, raltegravir potassium, tenofovir disoproxil, lamivudine, abacavir, zidovudine, emtricitabine, and a pharmaceutically acceptable salt of any of the foregoing.

7. The composition of claim 6, comprising two additional second agents independently selected from ritonavir, efavirenz, didanosine, raltegravir potassium, tenofovir disoproxil, lamivudine, abacavir, zidovudine, emtricitabine, and a pharmaceutically acceptable salt of any of the foregoing.

8. A method of treating HIV infection in a patient in need thereof comprising the step of administering to the patient an effective amount of a compound of claim 1.

9. The method of claim 8, further comprising administering to the patient a second therapeutic agent selected from a second HIV protease inhibitor, a non-nucleoside reverse transcriptase inhibitor, a nucleoside/nucleotide reverse transcriptase inhibitor, a viral entry inhibitor, an integrase inhibitor, an immune based antiretroviral agent, a viral maturation inhibitor, a cellular inhibitor, or combinations of two or more of the above.

10. The method of claim 9, wherein the second therapeutic agent is selected from ritonavir, efavirenz, didanosine, tenofovir disoproxil, nelfinavir mesilate, amprenavir, raltegravir potassium, saquinavir, lopinavir, nevirapine, emtricitabine, abacavir, lamivudine, zidovudine, maraviroc, stavudine, darunavir, fosamprenavir, vicriviroc, a pharmaceutically acceptable salt of any of the foregoing, and combinations thereof.

11. The method of claim 10, wherein the second therapeutic agent is selected from ritonavir, efavirenz, didanosine, raltegravir potassium, tenofovir disoproxil, lamivudine, abacavir, zidovudine, emtricitabine, a pharmaceutically acceptable salt of any of the foregoing, and combinations thereof.

12. The method of claim 11, further comprising administering to the patient two to three additional second therapeutic agents independently selected from ritonavir, efavirenz, didanosine, raltegravir potassium, tenofovir disoproxil, lamivudine, abacavir, zidovudine, emtricitabine, and a pharmaceutically acceptable salt of any of the foregoing.

13. The method of claim 12, further comprising administering to the patient two additional second agents independently selected from ritonavir, efavirenz, didanosine, raltegravir potassium, tenofovir disoproxil, lamivudine, abacavir, zidovudine, emtricitabine, and a pharmaceutically acceptable salt of any of the foregoing.

* * * * *

UNITED STATES PATENT AND TRADEMARK OFFICE
CERTIFICATE OF CORRECTION

| | | |
|---|---|---|
| PATENT NO. | : 8,258,309 B2 | Page 1 of 1 |
| APPLICATION NO. | : 13/411089 | |
| DATED | : September 4, 2012 | |
| INVENTOR(S) | : Scott L. Harbeson et al. | |

It is certified that error appears in the above-identified patent and that said Letters Patent is hereby corrected as shown below:

In the Claims:

Column 61, in Claim 2, Line 21: After the word "compound" insert the word --of--.
Column 61, in Claim 4, Line 31: Delete "aniprenavir" and replace with "amprenavir".

Signed and Sealed this
Eighth Day of January, 2013

David J. Kappos
*Director of the United States Patent and Trademark Office*